(12) United States Patent
Lencer et al.

(10) Patent No.: US 6,495,567 B1
(45) Date of Patent: *Dec. 17, 2002

(54) TRIARYL METHANE COMPOUNDS AND THEIR USE IN THE TREATMENT OF DIARRHEA AND SCOURS

(75) Inventors: Wayne I. Lencer, Jamaica Plains, MA (US); Carlo Brugnara, Newton Highlands, MA (US); Seth Alper, Jamaica Plain, MA (US)

(73) Assignees: Beth Israel Deaconess Medical Center, Boston, MA (US); Children's Medical Center Corporation, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/159,399

(22) Filed: Sep. 23, 1998

Related U.S. Application Data

(63) Continuation-in-part of application No. 08/621,169, filed on Mar. 20, 1996, now Pat. No. 5,889,038.

(51) Int. Cl.$^7$ ................ A61K 31/4429; A61K 31/4453; A61P 1/12

(52) U.S. Cl. .................... 514/317; 514/63; 514/75; 514/358; 514/648; 514/658; 514/663; 514/722; 514/724; 514/741; 514/748; 514/867

(58) Field of Search ........................ 514/867, 663, 514/724, 741, 748, 648, 658, 722, 63, 358, 75, 317

(56) References Cited

U.S. PATENT DOCUMENTS

| | | | |
|---|---|---|---|
| 3,917,615 A | * | 11/1975 | Adelstein |
| 4,806,685 A | | 2/1989 | Abraham et al. ............ 564/324 |
| 5,430,062 A | | 7/1995 | Cushman et al. ........... 514/646 |
| 5,889,038 A | * | 3/1999 | Lencer et al. ................ 514/396 |

FOREIGN PATENT DOCUMENTS

| | | |
|---|---|---|
| CA | 2186604 | 10/1995 |
| EP | 323740 | 7/1989 |
| EP | 583665 | 2/1994 |
| WO | WO 94/18967 | 9/1994 |
| WO | WO 95/26720 | 10/1995 |
| WO | WO 96/01107 | 1/1996 |
| WO | WO 97/34589 A | 9/1997 |
| WO | WO 97/34599 A | 9/1997 |
| WO | WO 99/25347 | 5/1999 |

OTHER PUBLICATIONS

Chemical Abstracts 119:63033j.

(List continued on next page.)

*Primary Examiner*—Edward J. Webman
(74) *Attorney, Agent, or Firm*—Wolf, Greenfield & Sacks, P.C.

(57) ABSTRACT

A method and product for treating and preventing diarrhea and scours is provided. The method involves treating a subject who has diarrhea, or scours, or is at risk of getting diarrhea or scours with an aromatic compound of the invention. The products of the invention are a veterinary preparation of the aromatic compound of the invention and an anti-scours agent, and a pharmaceutical preparation of the aromatic compound of the invention and an anti-diarrheal agent.

14 Claims, 2 Drawing Sheets

OTHER PUBLICATIONS

Li, et al., *Metal Based–Drugs*, 1996 3(5):241–242.
Paoletti, et al., *J. Neurosurg.*, 1971 34:454–455.
Simig, et al., *Tetrahedron*, 1978 34(15):2371–237.
O'Donnell, et al., *Bioorganic & Med. Chem.* 1995, 3(6):743–750.
Rideout, et al., *Anti–cancer Drug Design*, 1989 4(4):265–280.
Rideout, et al., *Int. J. Cancer*, 1994 57:247–253.
Paoletti, et al., *Advan. Exp. Med. Biol.*, 1969, 4:457–471.
Paoletti, et al., *Exp. Biol. of Brain Tumor*, 1972, 457–479.
Petersen, et al., *Bioorg. & Med. Chem.*, 1996, 4(7):1107–1112.
Rubright, et al., *Cancer Research*, 1967, 27:165–171.
Verheugen, et al., *Cell Calcium*, 1997, 21(1) 1–17.
Rader, et al., *Journal of Immunology*, vol. 156 (1996) pp. 1425–1430.

* cited by examiner

TRIARYL METHANE COMPOUNDS AND THEIR USE IN THE TREATMENT OF DIARRHEA AND SCOURS

CROSS-REFERENCE TO RELATED APPLICATIONS

This application is a continuation-in-part of application Ser. No. 08/621,169, filed Mar. 20, 1996, now U.S. Pat. No. 5,889,038, which is incorporated herein in its entirety by reference.

FIELD OF THE INVENTION

The present invention relates to methods and products for reducing chloride secretion using aromatic organic compounds. In particular the invention relates to methods of treating diarrhea and scours by administering triaryl methane compounds.

BACKGROUND OF THE INVENTION

Acute and chronic diarrheas represent a major medical problem in many areas of the world. Diarrhea is both a significant factor in malnutrition and the leading cause of death (5,000,000 deaths/year) in children less than five years old. Secretory diarrheas are also a dangerous condition in patients of acquired immunodeficiency syndrome (AIDS) and chronic inflammatory bowel disease (IBD). 16 million travelers to developing countries from industrialized nations every year develop diarrhea, with the severity and number of cases of diarrhea varying depending on the country and area of travel. The major medical consequences of diarrheal diseases include dehydration, acidosis, death and impaired growth.

Diarrhea in barn animals and pets such as cows, pigs and horses, sheep, goats, cats and dogs, also known as scours, is a major cause of death in these animals. Diarrhea can result from any major transition, such as weaning or physical movement. One form of diarrhea is characterized by diarrhea in response to a bacterial or viral infection and generally occurs within the first few hours of the animal's life.

Although the major consequences of diarrheal diseases are very similar, there are numerous causes of diarrhea. Secretory and exudative diarrhea are primarily caused by bacterial or viral infections. The most common diarrheal causing bacteria is enterotoxogenic *E-coli* (ETEC) having the K99 pilus antigen. Common viral causes of diarrhea include rotavirus and coronavirus. Other infectious agents include cryptosporidium, giardia lamblia, and salmonella, among others.

The treatment for diarrhea depends on the patient and the infection source. Diarrhea which is found in travelers to industrialized nations (travelers diarrhea) frequently is caused by bacterial pathogens which are acquired through ingestion of fecally contaminated food and/or water. Approximately 50–75% of these cases are attributed to ETEC. Although traveler's diarrhea is painful, it is generally not life-threatening and often the symptoms last only 3–5 days. The symptoms include urgent diarrhea, abdominal cramps, nausea and fever. The most effective course of treatment for traveler's diarrhea is the administration of antibiotics in conjunction with oral rehydration. It has been shown that prophylactic administration of antibiotics drastically reduces the number of travelers experiencing symptoms of diarrhea. However, routine administration of antibiotics is not suggested as it may cause resistant strains of a bacteria to develop. Other treatment methods include administration of bismuth subsalicylate, often taken in the form of Pepto-Bismal, diphenoxylate and loperamide.

Diarrhea in AIDS patients is a very serious condition which causes wasting and may be an important factor in the decline of these patients. AIDS patients often develop diarrhea due to enteric infections which their immune system is not capable of fighting off, but AIDS patients may also develop diarrhea by AIDS enteropathy. AIDS enteropathy is a disorder characterized by diarrhea without the involvement of secondary infections. It is caused by the human immunodeficiency virus (HIV) infection of the small bowel mucosal cells and colonic mucosal cells. The most common infective agent causing diarrhea due to enteric infection in AIDS patients in cryptosporidium. The methods for treating diarrhea in AIDS patients include administration of antibiotics and administration of immunoglobulins or an immunoglobulin enriched fraction of bovine colostrum. Colostrum, which is the first milk produced by mammals after birthing is enriched with antibodies.

Acute diarrhea or scours, is a main cause of death in many newborn barn animals such as calves and pigs. Scours is often caused by ETEC with a K99 pilus antigen. Infection with the ETEC causes hypersecretion of fluid and electrolytes. Hypersecretion in turn causes dehydration and pH imbalance which may result in death of the newborn calf or pig.

Newborn barn animals are also susceptible to viral infectious agents causing scours. Infections with rotavirus and coronavirus are common in newborn calves and pigs. Rotavirus infection often occurs within 12 hours of birth. Symptoms of rotaviral infection include excretion of watery feces, dehydration and weakness. Coronavirus which causes a more severe illness in the newborn animals, has a higher mortality rate than rotaviral infection. Often, however, a young animal may be infected with more than one virus or with a combination of viral and bacterial microorganisms at one time. This dramatically increases the severity of the disease.

Generally the best protection for a newborn barn animal from viral or bacterial infection is the consumption of colostrum. If the mother animal has been exposed to these infectious agents then the colostrum will contain antibodies, which are often sufficient to protect the newborn from contracting the diseases. Sometimes, however, this is not sufficient and the animals need further protection. A common method of treatment includes administration of a concentrated colostrum solution or an immunoglobulin fraction isolated from a colostrum solution. This oral treatment may be combined with rehydration salts. Although these methods have improved the morbidity and mortality rate of newborn animals having scours, there still exists a need for more effective treatments.

Certain imidazoles such as clotrimazole are agents which have been used both topically and systemically as antifungals. More recently, studies have identified other uses for such imidazoles. U.S. Pat. No. 5,273,992 revealed that these imidazoles regulate $Ca^{++}$ activated $K^+$ channels in erythrocytes, and are thus useful in treating sickle cell anemia, which involves the inhibition of potassium transport. These imidazoles have also been found to be effective in inhibiting endothelial and/or vascular smooth muscle cell proliferation. The results of this finding are described in U.S. Pat. No. 5,358,959 and U.S. Ser. No. 08/018,840, which discloses using clotrimazole for treating atherosclerotic and angiogenic conditions, respectively. Nonimidazole metabolites and analogs of the foregoing compounds also have been described as useful in treating the foregoing conditions (see U.S. Ser. Nos. 08/307,874 and 08/307,887).

SUMMARY OF THE INVENTION

The present invention provides methods and products for treating diarrhea and scours. It has been discovered that aromatic compounds are effective in treating patients with diarrhea and animals with scours. These compounds are potent inhibitors of secretagogue-stimulated transepithelial electrogenic chloride secretion in intestinal cells.

According to one aspect of the invention, a method for treating diarrhea of diverse etiology is provided. The method involves administering to a subject who is in need of such treatment, an aromatic compound of the invention in an amount effective to inhibit the diarrhea. Preferably the compound is administered orally in conjunction with oral rehydration fluids. The aromatic compounds useful in the invention have the following formula:

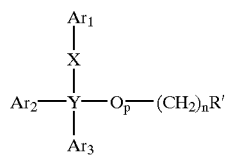
(I)

or a pharmaceutically acceptable salt or hydrate thereof, wherein: n is 0, 1, 2, 3 or 4; p is 0 or 1; X is absent, $(C_1-C_3)$alkyl, $(C_1-C_3)$alkenyl, $(C_1-C_3)$alkynyl, $SCH_2$, $OCH_2$, or $NOCH_2$, Y is C, N, P, Si or Ge; R' is absent, -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$, aryl, or heteroaryl; $Ar_1$ is aryl, substituted aryl, heteroaryl, $(C_5-C_8)$cycloalkyl or $(C_5-C_8)$heterocycloalkyl; $Ar_2$ is aryl or substituted aryl; $Ar_3$ is aryl, substituted aryl, biaryl, biphenyl, bibenzyl, or heteroaryl other than imidazole, nitroimidazole and triazole; each R is independently selected from the group consisting of —H, $(C_1-C_6)$alkyl, substituted $(C_1-C_6)$alkyl, $(C_1-C_6)$alkenyl, substituted $(C_1-C_6)$alkenyl($C_1-C_6$)alkynyl, substituted $(C_1-C_6)$alkynyl, and $(C_1-C_6)$alkoxy; the aryl substituents are each independently selected from the group consisting of -halo, trihalomethyl, —R, —$R_1$, —$OR_1$, —$SR_1$, $NR_{12}$, —$NO_2$, —CN, —C(O)$R_1$, —C(S)$R_1$, —C(O) $OR_1$, —C(S)$OR_1$, —C(O)$SR_1$ and —C(S)$SR_1$; the alkyl, alkenyl and alkynyl substituents are each independently selected from the group consisting of -halo, —$R_1$, —$OR_1$, —$SR_1$, $N(R_1)_2$, —$NO_2$, —CN, —C(O) $R_1$, —C(S)$R_1$, —C(O)$OR_1$, —C(S)$OR_1$, —C(O)$SR_1$, —C(S)$SR_1$, aryl, γ-butyrolactonyl, pyrrolidinyl and succinic anhydridyl; and each $R_1$ is independently selected from the group consisting of —H, $(C_1-C_6)$alkyl, $(C_1-C_6)$alkenyl and $(C_1-C_6)$alkynyl.

In a preferred embodiment p=0, X is absent, $(C_1-C_3)$ alkyl, $(C_1-C_3)$alkenyl, $(C_1-C_3)$ or alkynyl; R' is absent, —halo, —R, —OR, —SR, —$NR_2$, —$ONR_2$,—$NO_2$,—CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O) OR]$_2$, —CH[C(S)OR]$_2$, —CH[C(O)SR]$_2$, —CH[C(S)SR]$_2$, or aryl; $Ar_1$ is aryl, substituted aryl, heteroaryl other than imidazole, nitroimidazole and triazole, heteroarylium other than imidazolium, nitroimidazolium and triazolium, $(C_5-C_8)$ cycloalkyl or $(C_5-C_8)$heterocycloalkyl; $Ar_2$ is aryl or substituted aryl; and $Ar_3$ is aryl, substituted aryl, biaryl, or heteroaryl other than imidazole, nitroimidazole and triazole.

In a preferred embodiment the aromatic compounds are those of formula (I), except that the compounds are not any compound encompassed by formula (II):

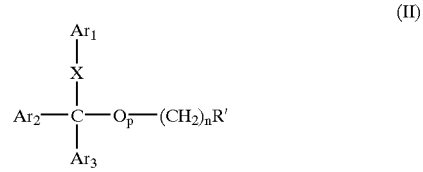
(II)

wherein n=0–3; wherein p=0 or 1; wherein X is selected from the group consisting of $(CH_2)_{m(m=0,1,2, \text{ or } 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R"$, OR", SR", NR"R", CONR"R", heteroaryl, and CONR"($OCH_3$); wherein $Ar_1$ is selected from the group consisting of phenyl, substituted phenyl, and heteroaryl; wherein $Ar_2$ is selected from the group consisting of phenyl and substituted phenyl; wherein $Ar_3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=1-5)}$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, SH, $SCH_3$, $NH_2$, $NHCH_3$, and $N(CH_3)_2$; and wherein R" is selected from the group consisting of hydrogen and R.

In one embodiment of the invention the foregoing aromatic compounds may be administered in combination with other non-formula (I) anti-diarrheal agents. In another embodiment the aromatic compounds may be administered in combination with other non-formula (I) anti-scours agents.

According to one embodiment of the invention the subject in need of such treatment is a subject who has symptoms of diarrhea or scours. In another embodiment of the invention, the subject in need of such treatment is a subject at risk of developing diarrhea or scours.

In general diarrhea is a secretory disorder, which is caused by at least one of several mechanisms. In one embodiment the diarrhea is an exudative form of diarrhea; In one embodiment the diarrhea is a nonexudative form of diarrhea; In another embodiment the diarrhea is a decreased absorption form of diarrhea; In another embodiment the diarrhea is a non-decreased absorption form of diarrhea; In yet another embodiment the diarrhea is a secretory form of diarrhea. In yet another embodiment the diarrhea is a nonsecretory form of diarrhea. In still another embodiment the diarrhea is a noninflammatory form of diarrhea.

According to another aspect of the invention, pharmaceutical preparations are provided. These pharmaceutical preparations include the aromatic compounds of the invention together with an anti-diarrheal agent. In one embodiment, the aromatic compounds useful according to the invention have the general formula (I) provided above. In another embodiment, the aromatic compounds useful according to the invention have the general formula (I) provided above but do not include the compounds of formula (II). In yet another embodiment, the aromatic compounds useful according to the invention have the above-disclosed general formula (I), but wherein R' and $Ar_1$ do not include imidazoles. Preferably the pharmaceutical composition of the invention may be administered orally.

According to another aspect of the invention, veterinary preparations are provided. These veterinary preparations include the aromatic compounds useful according to the invention together with an anti-scours preparation. In one embodiment, the aromatic compounds useful according to the invention have the general formula (I) provided above. In another embodiment, the aromatic compounds useful according to the invention have the general formula (I) provided above but do not include the compounds of formula (II). In yet another embodiment, the aromatic compounds useful according to the invention have the above-disclosed general formula (I), but wherein R' and $Ar_1$ do not include imidazoles.

The invention also provides the aromatic compounds of the invention in the manufacture of a medicament for the treatment of diarrhea. In one embodiment, the aromatic compounds of the invention have the above-disclosed general formula, but do not include clotrimazole. In another embodiment, the aromatic compounds useful in the manufacture of a medicament for the treatment of diarrhea have the above-disclosed general formula, but wherein R' and $Ar_1$ do not include imidazoles.

The invention also provides the aromatic compounds of the invention in the manufacture of a medicament for the treatment of scours. In one embodiment, the aromatic compounds of the invention have the general formula (I). In another embodiment, the aromatic compounds useful in the manufacture of a medicament for the treatment of scours have the general formula (I) provided above but do not include the compounds of formula (II).

In embodiments of each of the methods or products of the invention the aromatic compounds have the following the structural formula (III):

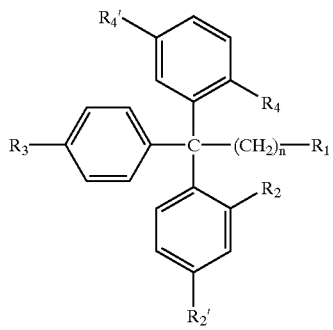

(III)

wherein:

n is 0, 1, 2, 3 or 4;

$R_1$ is —H, —OR, —SR, —CN, —C(O)R, —C(O)OR, —C(O)NR$_2$, —CH[C(O)R]$_2$ or —CH[C(O)OR]$_2$;

$R_2$ is —F, —Cl, —Br, —I, —OR, —SR, —C(O)R or —C(O)NR$_2$;

$R_{2'}$ is —H or —NO$_2$;

$R_3$ is —H, ($C_1$–$C_6$)alkyl, ($C_1$–$C_6$)alkenyl, ($C_1$–$C_6$)alkynyl, —OR or —SR;

$R_4$ is —H or —NR$_2$;

$R_{4'}$ is —H, —F, —Cl, —Br or —I; and each R is independently selected from the group consisting of —H, ($C_1$–$C_6$) alkyl, ($C_1$–$C_6$)alkenyl, ($C_1$–$C_6$)alkynyl or ($C_1$–$C_6$)alkoxy.

In another preferred embodiment, the aromatic compounds of the invention are compounds having the structural formula (IV):

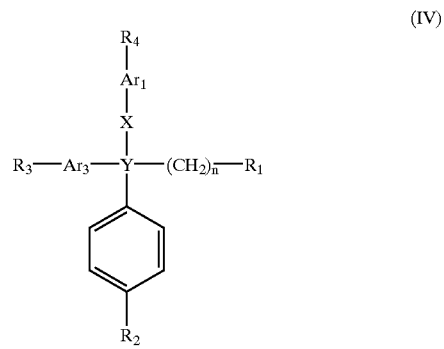

(IV)

wherein:

X is absent or —C≡C—;

Y is C, P, Si or Ge;

n is 0, 1, 2, 3 or 4;

$Ar_1$ is phenyl, substituted phenyl, cycloalkyl or heteroarylium other than imidazolium, nitroimidazolium or triazolium;

$Ar_3$ is phenyl, naphthyl, piperidyl or cyclohexyl;

$R_1$ is —R, —OR, —SR, —CN, —NR$_2$, —ONR$_2$, —C(O)R, —C(O)OR, —C(O)NR$_2$, —CH[C(O)R]$_2$, —CH[C(O)OR]$_2$, ($C_1$–$C_6$)alkyl, ($C_1$–$C_6$)alkenyl, ($C_1$—$C_6$)alkynyl, cyclopenta-2,4-diene-1-ylidene or phenyl;

each of $R_2$, $R_3$ and $R_4$ is independently selected from the group consisting of —H, —F, —Cl, —Br, —I, —OR, —SR, —NR$_2$, —NO$_2$, —C(O)R, —C(O)OR, —C(O)NR$_2$, trihalomethyl, ($C_1$–$C_6$)alkyl, ($C_1$–$C_6$)alkenyl, ($C_1$–$C_6$)alkynyl and phenyl;

each R is independently selected from the group consisting of —H, halo, ($C_1$–$C_6$)alkyl, substituted ($C_1$–$C_6$) alkyl, ($C_1$–$C_6$)alkenyl, substituted ($C_1$–$C_6$)alkenyl, ($C_1$–$C_6$)alkynyl, substituted ($C_1$–$C_6$)alkynyl and ($C_1$–$C_6$)alkoxy;

the alkyl, alkenyl or alkynyl substituents are each independently selected from the group consisting of aryl, —C(O)OR, pyrrolidinyl, butyrolactonyl, —F, —Cl, —Br, —I and —CN; and the phenyl substituents are each independently —R.

In another preferred embodiment, the aromatic compounds of the invention are compounds having the formula (V):

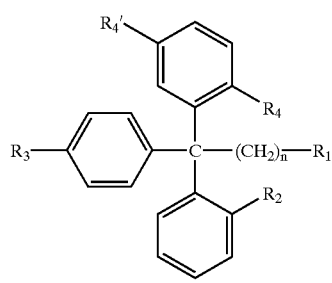

(V)

or pharmaceutically acceptable salts or hydrates thereof, wherein:

n is 0, 1, 2, 3 or 4;

R is —H, —OR, —SR, —CN, —C(O)R, —C(S)R, —C(O)OR, —C(S)OR, —C(O)SR, —C(S)SR, —C(O)NR$_2$, —C(S)NR$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$;

R$_2$ is —F, —Cl, —Br or —I;

R$_3$ is —R, —OR or —SR;

R$_4$ is —H or —NR$_2$;

R$_{4'}$ is —H, —F, —Cl, —Br or —I; and each R is independently selected from the group consisting of —H, (C$_1$–C$_6$)alkyl, (C$_1$–C$_6$)alkenyl, (C$_1$–C$_6$) alkynyl and (C$_1$–C$_6$)alkoxy.

In another preferred embodiment, the compounds of the invention are those of formula (V), with the provisos that (i) when n is 0 and R$_1$ is —H or —OH, R$_3$ is other than —H; and (ii) when n is 0 and R$_1$ is —H, R$_3$ is other than —OH.

In another preferred embodiment, the compounds of the invention are those of formula (V), with the proviso that when n is 0 and R$_1$ is —C(O)NH$_2$, R$_2$ is other than —F.

In another preferred embodiment, the aromatic compounds of the invention are compounds having the formula (VI):

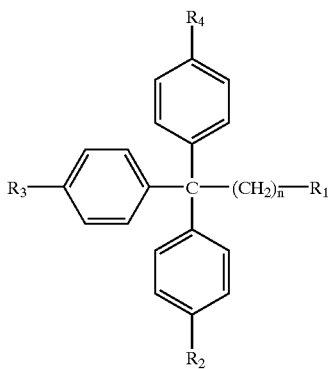

(VI)

or pharmaceutically acceptable salts or hydrates thereof, wherein:

n is 0, 1, 2, 3 or 4;

R$_1$ is —NR$_2$, —C(O)R, —C(S)R, —C(O)NR'$_2$ or —C(S)NR'$_2$;

R$_2$ is —F, —Cl, —Br or —I;

R$_3$ is —F, —Cl, —Br or —I;

R$_4$ is —F, —Cl, —Br or —I;

each R is independently selected from the group consisting of —H, (C$_1$–C$_6$)alkyl, (C$_1$–C$_6$)alkenyl, (C$_1$–C$_6$) alkynyl and (C$_1$–C$_6$)alkoxy; and each R' is independently selected from the group consisting of —H, (C$_1$–C$_6$)alkyl, (C$_1$–C$_6$)alkenyl, (C$_1$–C$_6$) alkynyl and (C$_1$–C$_6$)alkoxy.

In another preferred embodiment, the compounds of the invention are compounds having the formula (VII):

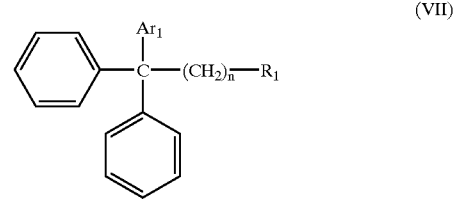

(VII)

or pharmaceutically acceptable salts or hydrates thereof, wherein:

n is 0, 1, 2, 3 or 4;

Ar$_1$ is phenyl or cyclohexyl;

R, is —NR$_2$, —CH[C(O)OR]$_2$, —CH[C(S)OR]$_2$, —CH[C(O)SR]$_2$, —CH[C(S)SR]$_2$, —C(O)NR$_2$ or —C(S)NR$_2$; and each R is independently selected from the group consisting of —H, (C$_1$–C$_6$)alkyl, (C$_1$–C$_6$)alkenyl, (C$_1$–C$_6$) alkynyl and (C$_1$–C$_6$)alkoxy.

Each of the limitations of the invention can encompass various embodiments of the invention. It is, therefore, anticipated that each of the limitations of the invention involving any one element or combinations of elements can be included in each aspect of the invention.

DETAILED DESCRIPTION OF THE INVENTION

Figure 1:
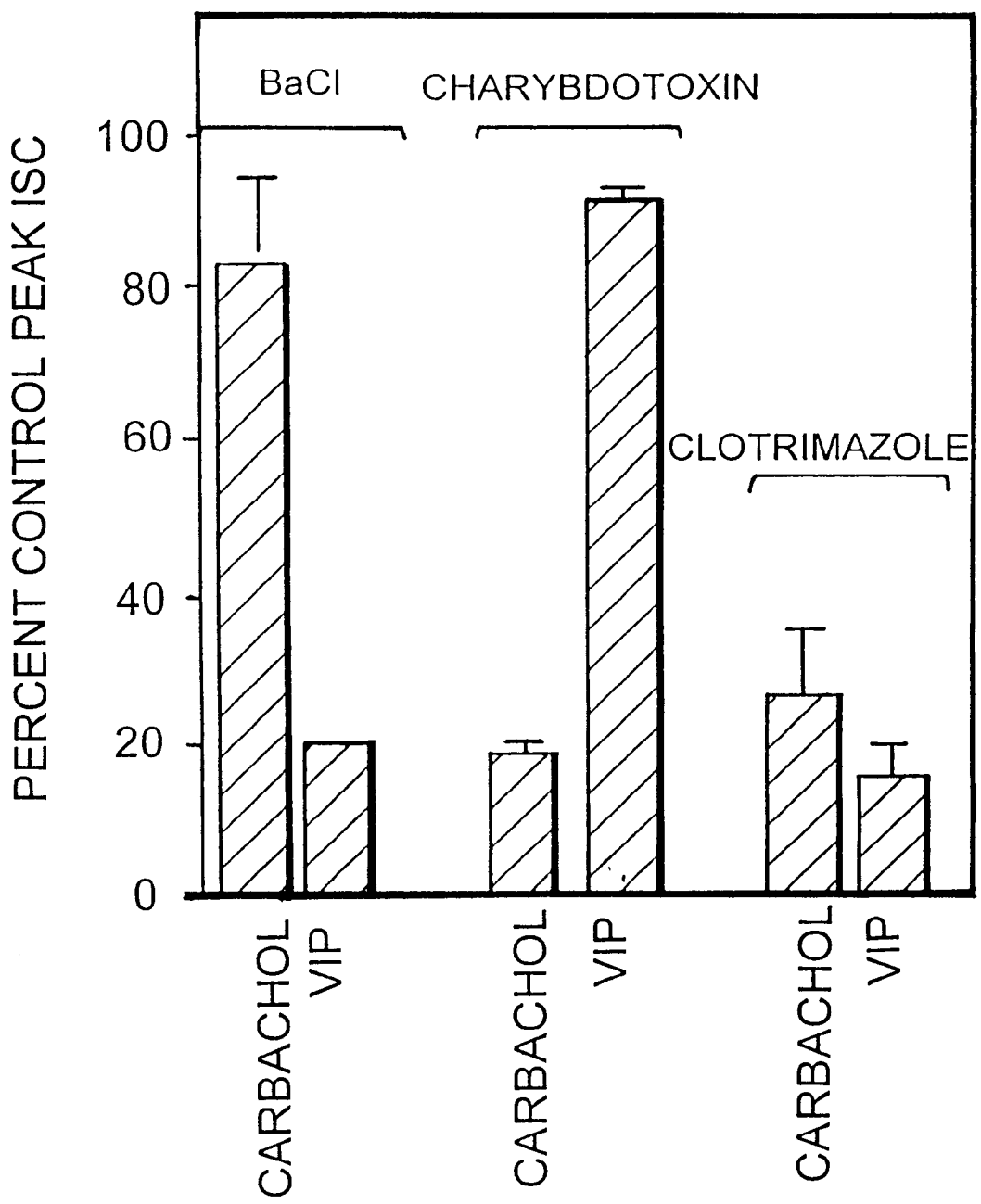
FIG. 1 is a bar graph depicting the effect of clotrimazole in the inhibition of cAMP and Ca$^{++}$ dependent Cl$^-$ secretion in T84 cells.
Figure 2:
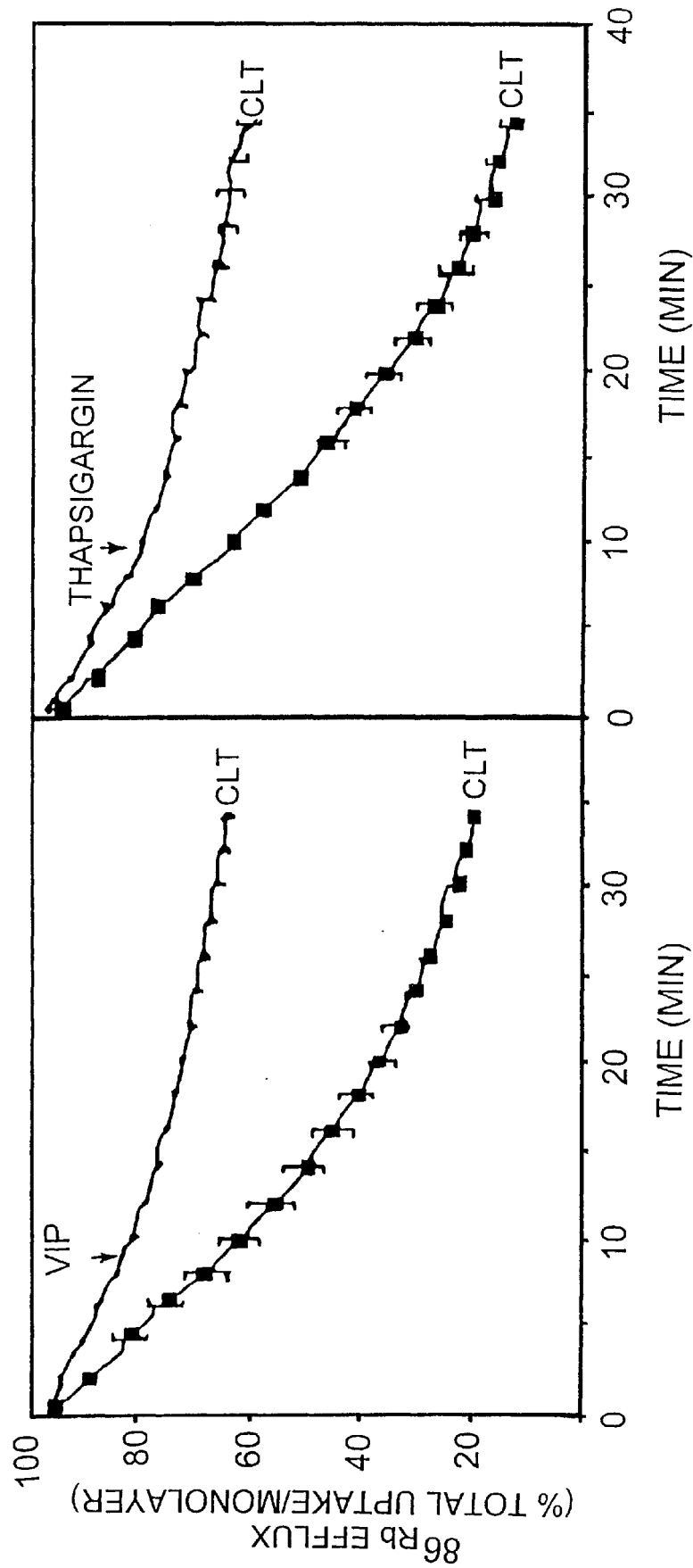
FIG. 2 is a graph showing the effect of clotrimazole on the inhibition of base line and Ca$^{++}$-stimulated $^{86}$Rb efflux from T84 monolayers.

The invention involves methods and products for reducing the symptoms of diarrhea or preventing diarrhea in a subject at risk for developing diarrhea. The compounds of the invention are aromatic compounds. The aromatic compounds useful according to the invention may be provided in a pharmaceutical preparation or a veterinary preparation. The aromatic compounds of the invention are also useful in a method for treating diarrhea and scours as well as a method for preventing diarrhea and scours.

The aromatic compounds useful in the invention have the following formula (I):

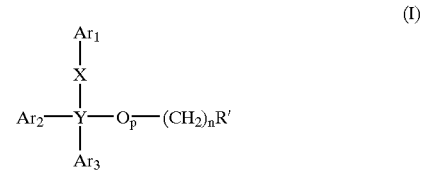

(I)

or a pharmaceutically acceptable salt or hydrate thereof, wherein: n is 0, 1, 2, 3 or 4; p is 0 or 1; X is absent, (C$_1$–C$_3$)alkyl, (C$_1$–C$_3$)alkenyl, (C$_1$–C$_3$)alkynyl, SCH$_2$, OCH$_2$, or NOCH$_2$; Y is C, N, P, Si or Ge; R' is absent, -halo, —R, —OR, —SR, —NR$_2$, —ONR$_2$, —NO$_2$, —CN, —C(O)R, —C(S)R, —C(O)OR, —C(S)OR, —C(O)SR, —C(S)SR, —C(O)NR$_2$, —C(S)NR$_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$, aryl, or heteroaryl; Ar$_1$ is aryl, substituted aryl, heteroaryl, (C$_5$–C$_8$)cycloalkyl or (C$_5$–C$_8$)heterocycloalkyl; Ar$_2$ is aryl or substituted aryl; Ar$_3$ is aryl, substituted aryl, biaryl, biphenyl, bibenzyl, or heteroaryl other than imidazole, nitroimidazole and triazole; each R is independently selected from the group consisting of —H, (C$_1$–C$_6$)alkyl, substituted (C$_1$–C$_6$)alkyl, (C$_1$–C$_6$)alkenyl, substituted (C$_1$–C$_6$)alkenyl (C$_1$–C$_6$)alkynyl, substituted (C$_1$–C$_6$) alkynyl, and (C$_1$–C$_6$)alkoxy; the aryl substituents are each independently selected from the group consisting of -halo, trihalomethyl, —R, —R$_1$, —OR$_1$, —SR$_1$, NR$_{12}$, —NO$_2$, —CN, —C(O)R$_1$, —C(S)R$_1$, —C(O)OR$_1$, —C(S)OR$_1$, —C(O)SR$_1$ and —C(S)SR$_1$; the alkyl, alkenyl and alkynyl substituents are each independently selected from the group consisting of -halo, —R$_1$, —OR$_1$, —SR$_1$, N(R$_1$)$_2$, —NO$_2$, —CN, —C(O)R$_1$, —C(S)R$_1$, —C(O)OR$_1$, —C(S)OR$_1$, —C(O)SR$_1$, —C(S)SR$_1$, aryl, γ-butyrolactonyl, pyrrolidinyl and succinic anhydridyl; and each R$_1$ is independently selected from the group consisting of —H, (C$_1$–C$_6$) alkyl, (C$_1$–C$_6$)alkenyl and (C$_1$–C$_6$)alkynyl.

In a preferred embodiment p=0, X is absent, (C$_1$–C$_3$) alkyl, (C$_1$–C$_3$)alkenyl, (C$_1$–C$_3$) or alkynyl; R' is absent, -halo, —R, —OR, —SR, —NR$_2$, —ONR$_2$, —NO$_2$, —CN, —C(O)R, —C(S)R, —C(O)OR, —C(S)OR, —C(O)SR, —C(S)SR, —C(O)NR$_2$, —C(S)NR$_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$, or aryl; Ar$_1$ is aryl, substituted aryl, heteroaryl other than imidazole, nitroimidazole and triazole, heteroarylium other than imidazolium, nitroimidazolium and triazolium, (C$_5$–C$_8$) cycloalkyl or (C$_5$–C$_8$) heterocycloalkyl; Ar$_2$ is aryl or substituted aryl; and Ar$_3$ is aryl, substituted aryl, biaryl, or heteroaryl other than imidazole, nitroimidazole and triazole.

In a preferred embodiment the aromatic compounds are those of formula (I), except that the compounds are not any compound encompassed by formula (II):

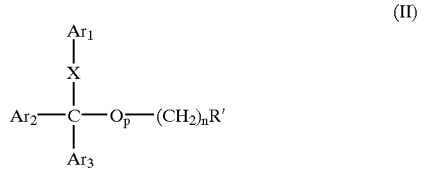

(II)

wherein n=0–3; wherein p=0 or 1; wherein X is selected from the group consisting of (CH$_2$)$_{m(m=0,1,2, or 3)}$, CH=CH, C≡C, SCH$_2$, OCH$_2$, and NOCH$_2$; wherein R' is selected from the group consisting of H, OH, SH, NO$_2$, CN, CHO, ONH$_2$, CCH, COR", CO$_2$H, CO$_2$R", OR", SR", NR"R", CONR"R", heteroaryl, and CONR"(OCH$_3$); wherein Ar$_1$ is selected from the group consisting of phenyl, substituted phenyl, and heteroaryl; wherein Ar$_2$ is selected from the group consisting of phenyl and substituted phenyl; wherein Ar$_3$ is selected from the group consisting of phenyl, substituted phenyl, biphenyl, bibenzyl, and naphthyl; wherein the phenyl substituent is selected from the group consisting of Cl, F, Br, I, R, OR", SR", NO$_2$, CN, CF$_3$, NR"R", and CO$_2$R; wherein R is selected from the group consisting of straight chain alkyl of C$_{z(z=1-5)}$, substituted straight chain alkyl of C$_{z(z=1-5)}$, branched alkyl of C$_{z(z=1-5)}$, and substituted branched alkyl of C$_{z(z=1-5)}$; wherein the alkyl substituent is selected from the group consisting of Cl, Br, F, I, OH, OCH$_3$, SH, SCH$_3$, NH$_2$, NHCH$_3$, and N(CH$_3$)$_2$; and wherein R" is selected from the group consisting of hydrogen and R.

As used herein, the term "alkyl" refers to a saturated branched, straight chain or cyclic hydrocarbon radical. Typical alkyl groups include methyl, ethyl, propyl, isopropyl, cyclopropyl, butyl, isobutyl, t-butyl, cyclobutyl, pentyl, isopentyl, cyclopentyl, hexyl, cyclohexyl and the like.

As used herein, the term "heterocycloalkyl" refers to a saturated cyclic hydrocarbon radical wherein one or more of the carbon atoms is replaced with another atom such as Si, Ge, N, O, S or P. Typical heterocycloalkyl groups include, but are not limited to, morpholino, thiolino, piperidyl, pyrrolidinyl, piperazyl, pyrazolidyl, imidazolidinyl, and the like.

As used herein, the term "alkenyl" refers to an unsaturated branched, straight chain or cyclic hydrocarbon radical having at least one carbon-carbon double bond. The radical may be in either the cis or trans conformation about the double bond(s). Typical alkenyl groups include ethenyl, propenyl, isopropenyl, cyclopropenyl, butenyl, isobutenyl, cyclobutenyl, tert-butenyl, pentenyl, hexenyl and the like.

As used herein, the term "alkynyl" refers to an unsaturated branched, straight chain or cyclic hydrocarbon radical having at least one carbon-carbon triple bond. Typical alkynyl groups include ethynyl, propynyl, butynyl, isobutynyl, pentynyl, hexynyl and the like.

As used herein, the term "alkoxy:" refers to an —OR radical, where R is alkyl, alkenyl or alkynyl, as defined above.

As used herein, the term "aryl" refers to an unsaturated cyclic hydrocarbon radical having a conjugated π electron system. Typical aryl groups include, but are not limited to, penta-2,4-diene, phenyl, naphthyl, anthracyl, azulenyl, indacenyl, and the like.

As used herein, the term "heteroaryl" refers to an aryl group wherein one or more of the ring carbon atoms is replaced with another atom such as N, O or S. Typical heteroaryl groups include, but are not limited to,furanyl, imidazole, pyridinyl, thiophenyl, indolyl, imidazolyl, quinolyl, thienyl, indolyl, pyrrolyl, pyranyl, pyridyl, pyrimidyl, pyrazyl, pyridazyl, and the like.

As used herein, the term "heteroarylium" refers to a heteroaryl group wherein one or more hydrogens has been added to any position of the neutral parent ring. Typical heteroarylium groups include, but are not limited to, pyridinium, pyrazinium, pyrimidinium, pyridazinium, 1,3, 5-triazinium, and the like.

As used herein, the term "in situ" refers to and includes the terms "in vivo," "ex vivo," and "in vitro" as these terms are commonly recognized and understood by persons ordinarily skilled in the art. Moreover, the phrase "in situ" is employed herein in its broadest connotative and denotative contexts to identify an entity, cell or tissue as found or in place, without regard to its source or origin, its condition or status or its duration or longevity at that location or position.

In one embodiment, the substituents of the aromatic compounds of formula (I) are as follows:

n is 0, 1, 2, 3 or 4;

X is absent or —C≡C—;

Y is C, N, P, Si or Ge;

R$_1$ is absent, —F, —Cl, —Br, —R, —OR, —SR, —NR$_2$, —ONR$_2$, —NO$_2$, —CN, —C(O)R, —C(O)OR, —C(O)NR$_2$, —C(O)NR(OR), —CH[C(O)OR]$_2$ or cyclo-penta-2,4-dien-1-ylidene;

Ar$_1$ is phenyl, substituted phenyl, heteroaryl other than imidazole, nitroimidazole and triazole, cyclohexyl, piperidyl or pyridinium;

Ar$_2$ is phenyl or substituted phenyl;

Ar$_3$ is phenyl, substituted phenyl, biphenyl, naphthyl or pyridyl;

R is —H, (C$_1$–C$_3$)alkyl, substituted (C$_1$–C$_3$)alkyl, (C$_1$–C$_3$)alkenyl, substituted (C$_1$–C$_3$)alkenyl (C$_1$–C$_3$) alkynyl, substituted (C$_1$–C$_3$)alkynyl and (C$_1$–C$_3$) alkoxy;

the phenyl substituents are each independently selected from the group consisting of —F, —Cl, —Br, —CF$_3$, —R, —R', —OR', —SR', NR'$_2$, —NO$_2$, —CN, —C(O)R' and —C(O)OR';

the alkyl, alkenyl and alkynyl substituents are each independently selected from the group consisting of —F, —Cl, —Br, —R', —OR', —SR', NR'$_2$, —NO$_2$, —CN, —C(O)R', —C(O)OR', naphthyl, γ-butyrolactonyl and pyrrolidinyl; and each R' is independently selected from the group consisting of —H, (C$_1$–C$_3$)alkyl, (C$_1$–C$_3$)alkenyl and (C$_1$–C$_3$) alkynyl.

Exemplary preferred aromatic compounds according to formula (I) include those listed in TABLE A, below.

TABLE A

Exemplary Compounds

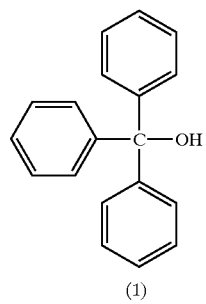

(1)

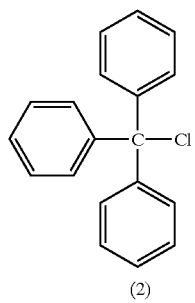

(2)

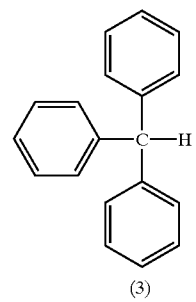

(3)

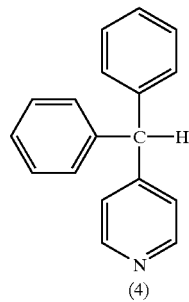

(4)

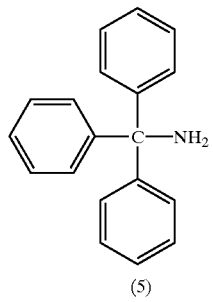

(5)

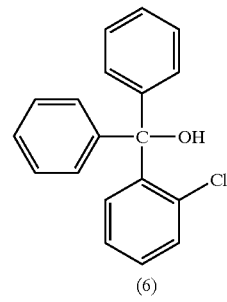

(6)

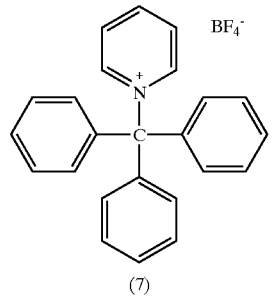

(7)

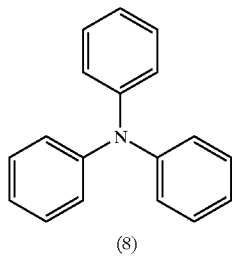

(8)

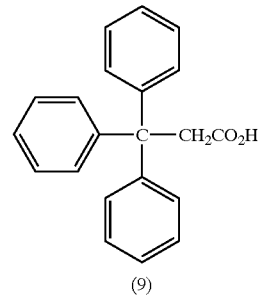

(9)

TABLE A-continued
Exemplary Compounds
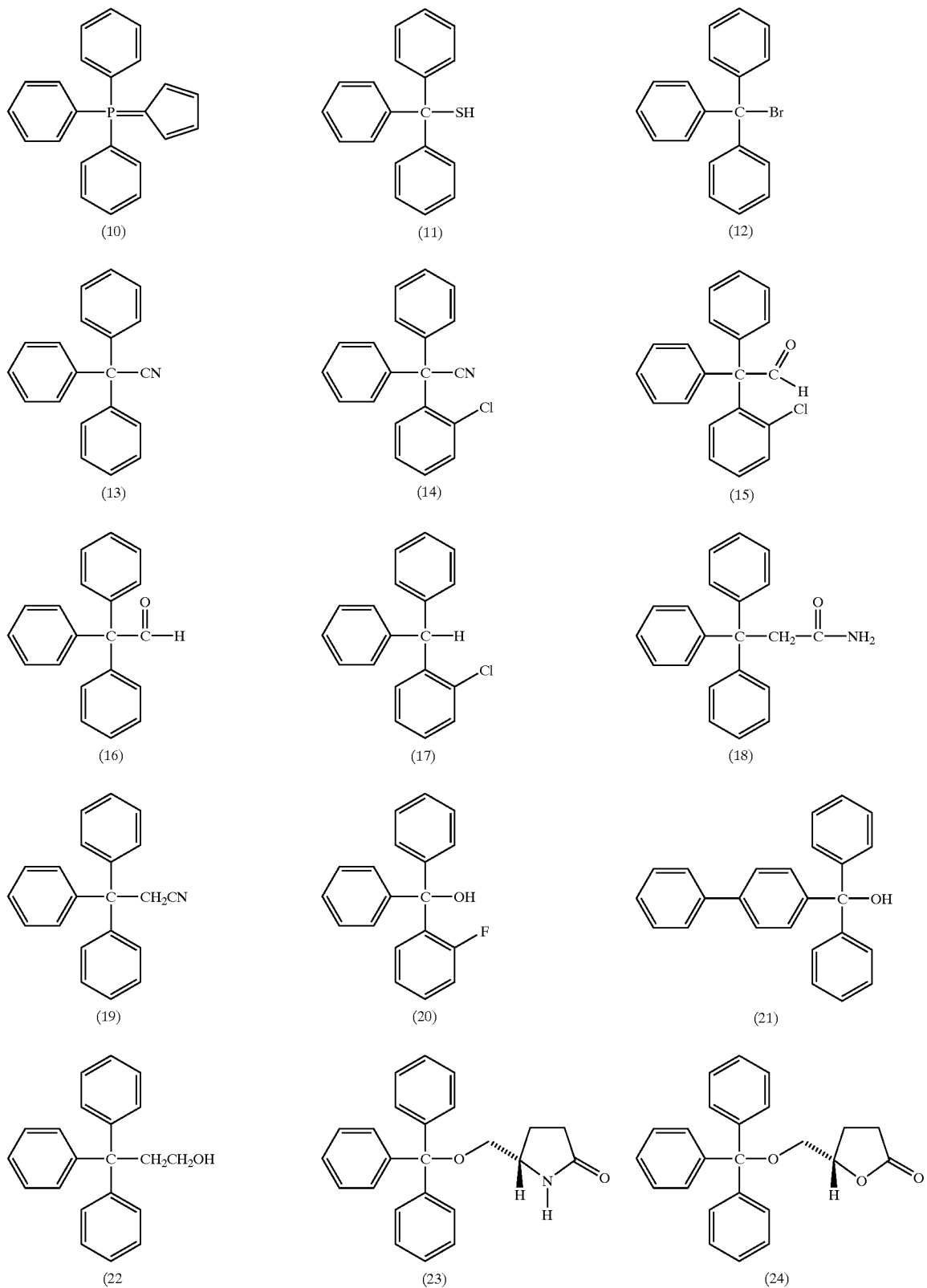

TABLE A-continued
Exemplary Compounds
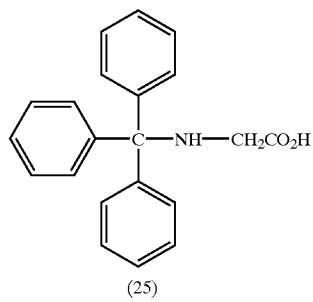
(25)
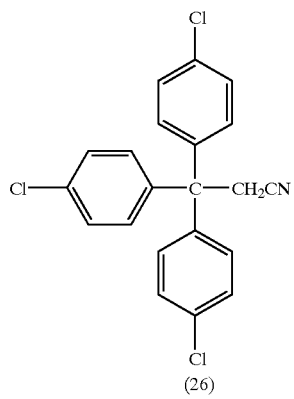
(26)
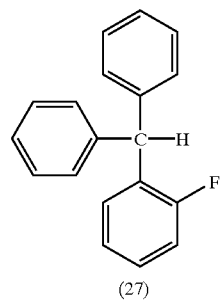
(27)
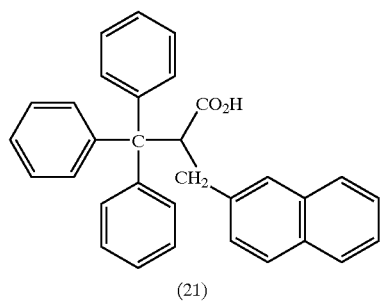
(21)
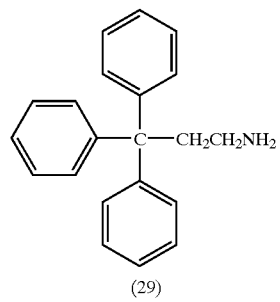
(29)
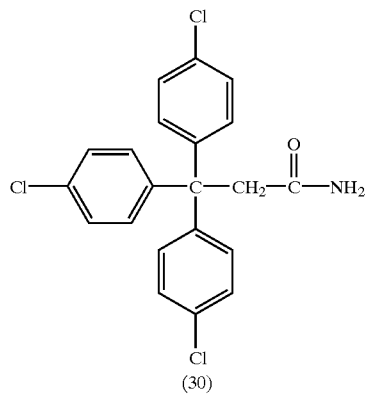
(30)
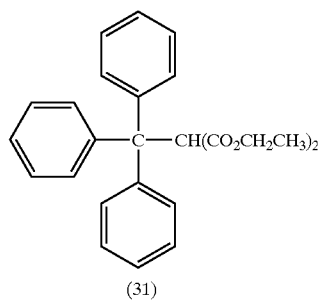
(31)
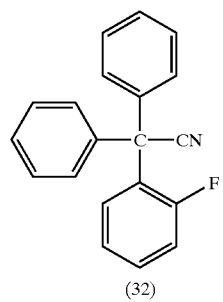
(32)
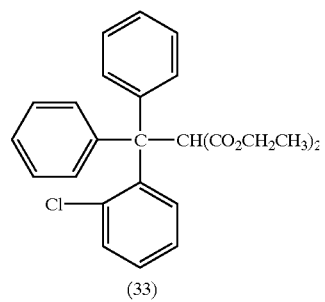
(33)
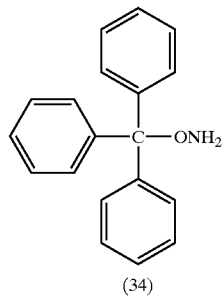
(34)
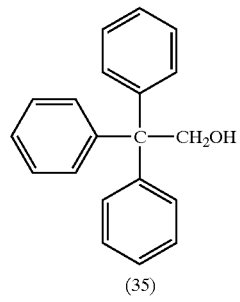
(35)
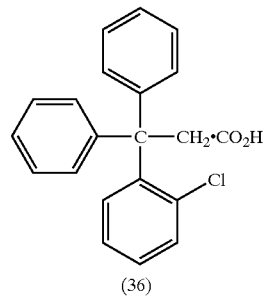
(36)

TABLE A-continued
Exemplary Compounds
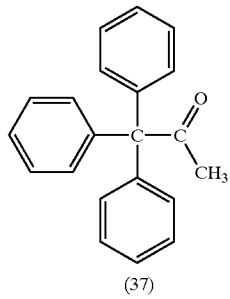
(37)
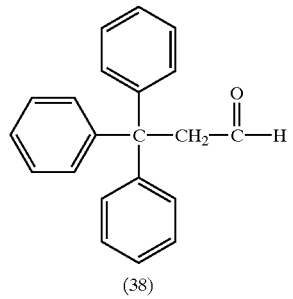
(38)
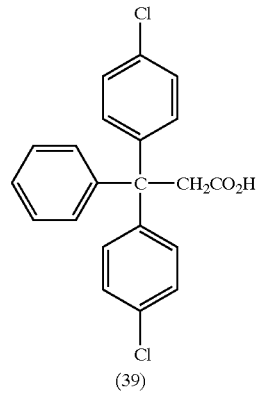
(39)
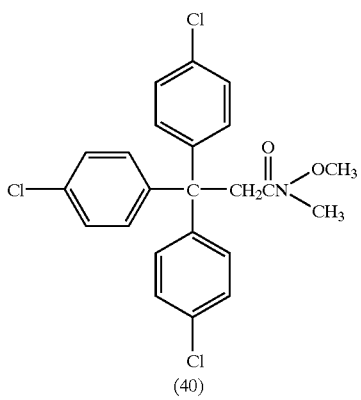
(40)
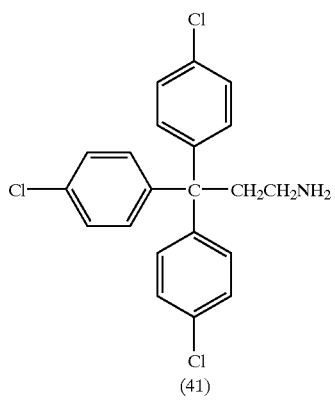
(41)
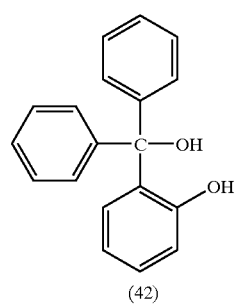
(42)
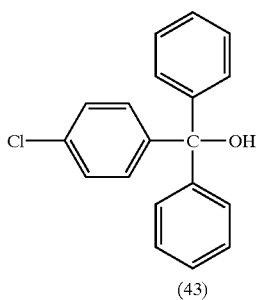
(43)
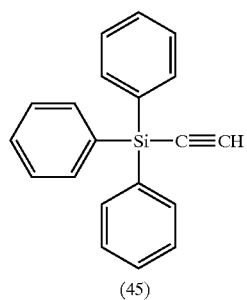
(45)
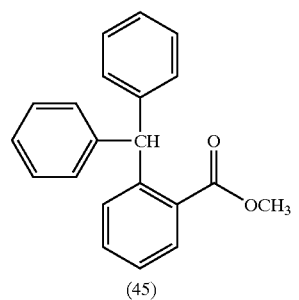
(45)
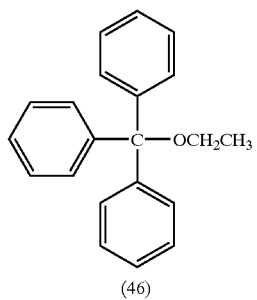
(46)
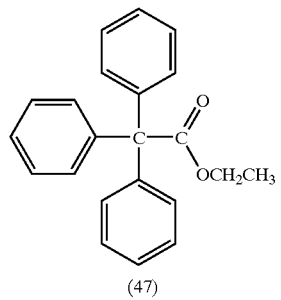
(47)
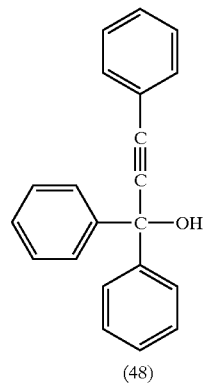
(48)

TABLE A-continued
Exemplary Compounds
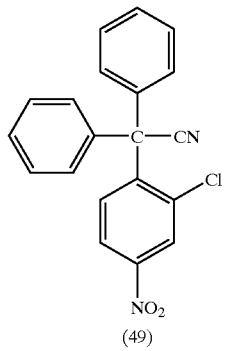
(49)
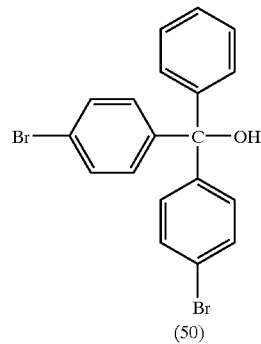
(50)
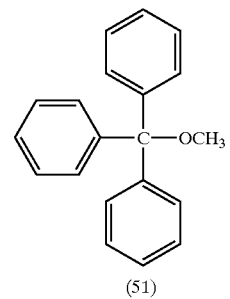
(51)
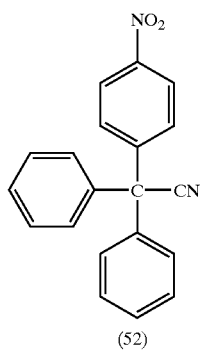
(52)
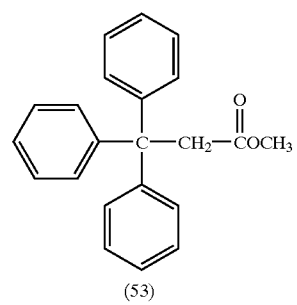
(53)
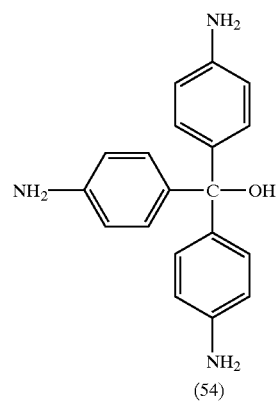
(54)
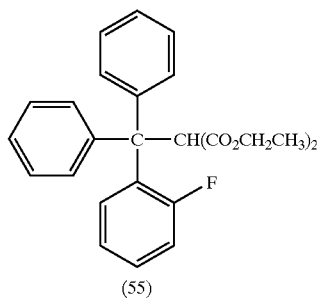
(55)
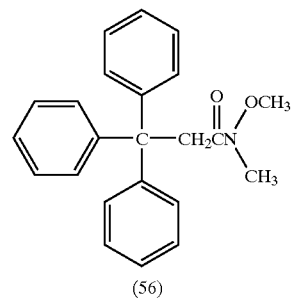
(56)
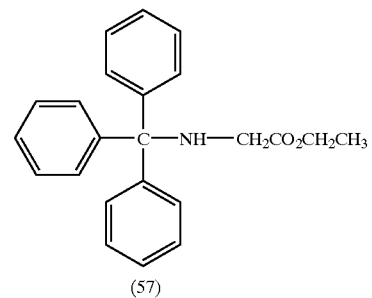
(57)
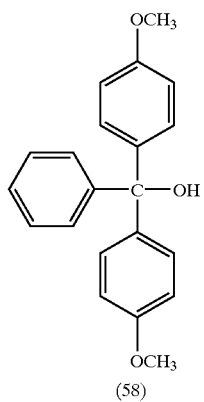
(58)
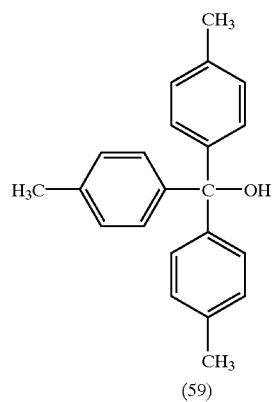
(59)
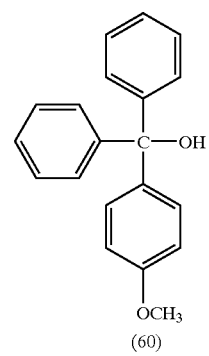
(60)

TABLE A-continued
Exemplary Compounds
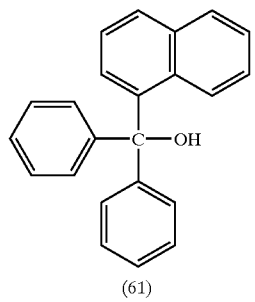
(61)
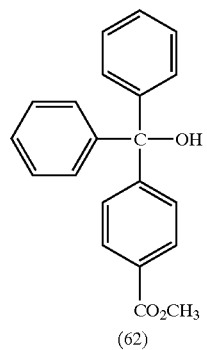
(62)
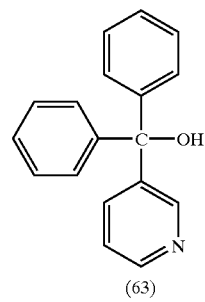
(63)
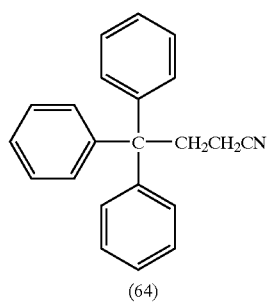
(64)
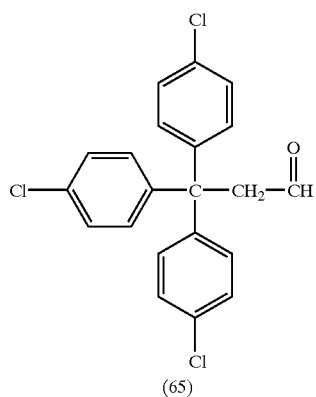
(65)
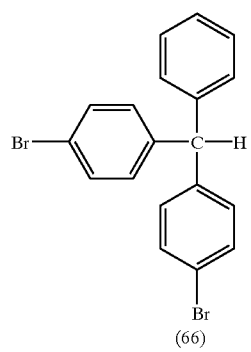
(66)
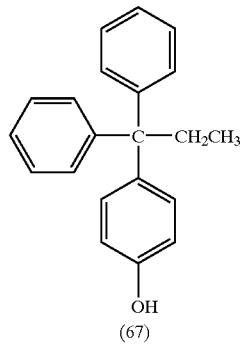
(67)
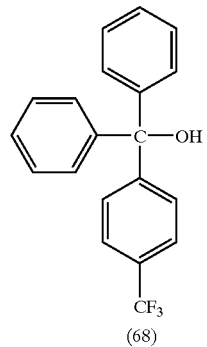
(68)
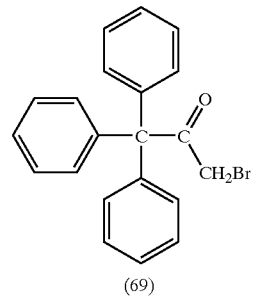
(69)
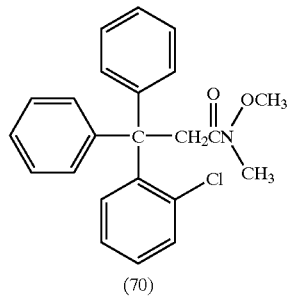
(70)
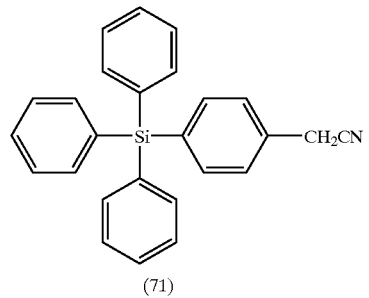
(71)
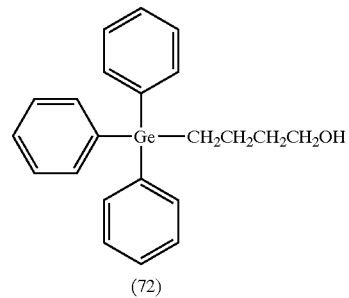
(72)

TABLE A-continued
Exemplary Compounds
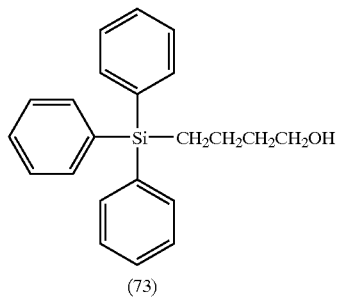
(73)
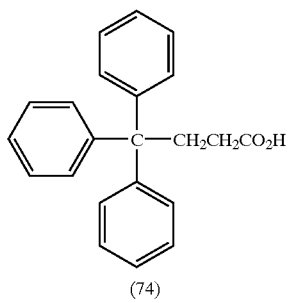
(74)
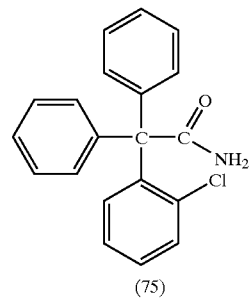
(75)
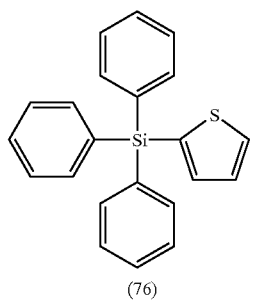
(76)
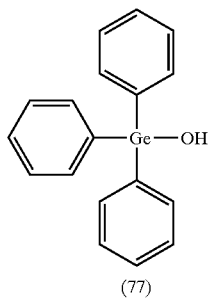
(77)
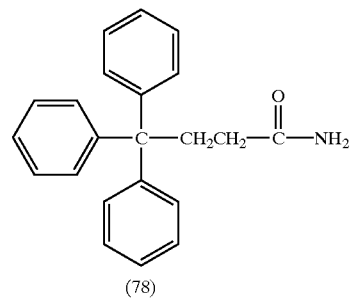
(78)
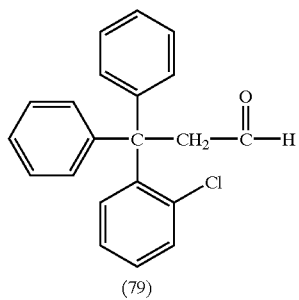
(79)
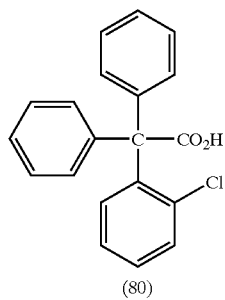
(80)
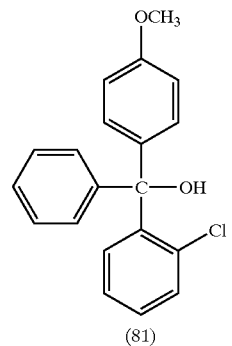
(81)
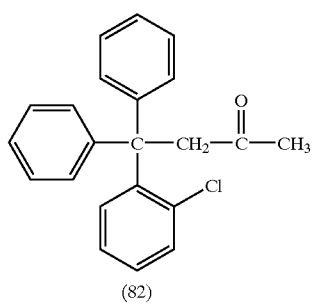
(82)
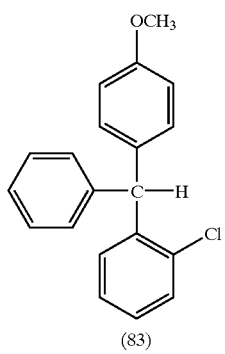
(83)
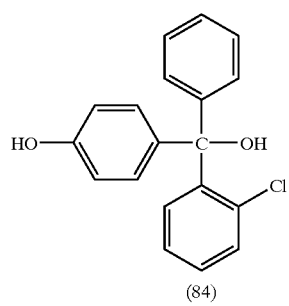
(84)

TABLE A-continued

Exemplary Compounds

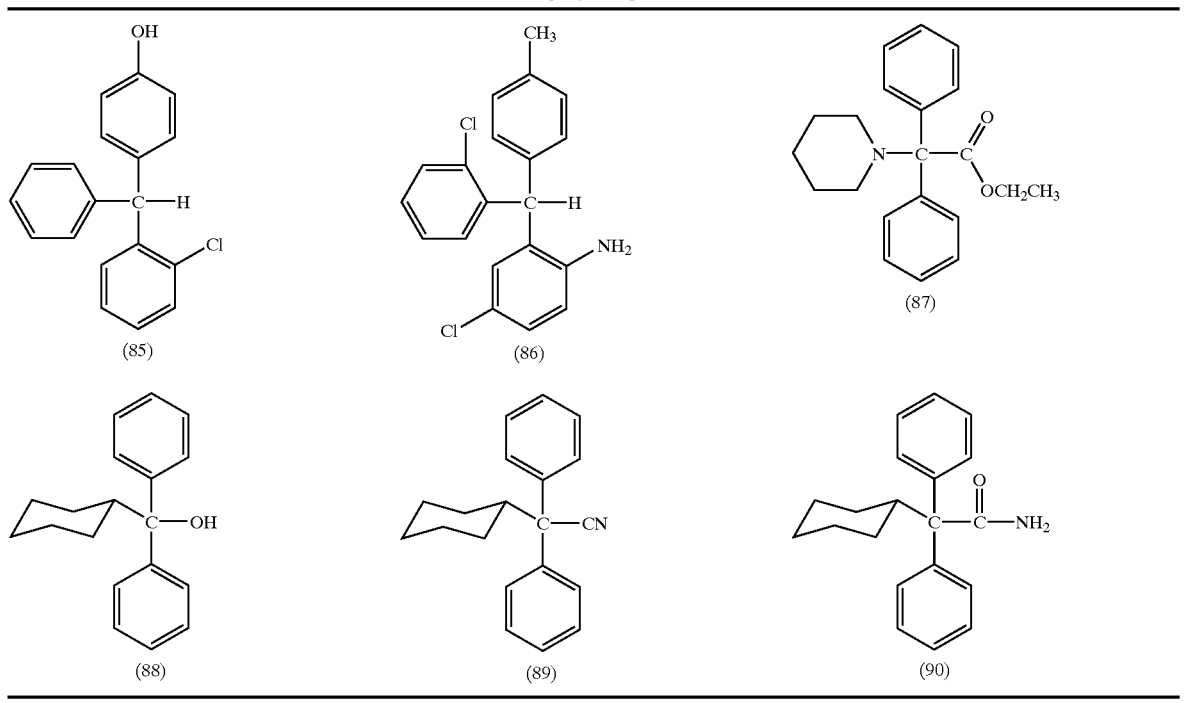

The compounds will be referred to herein by way of compound numbers as presented in TABLE A, above.

Other aromatic compounds believed useful according to the invention are compounds having the structural formula (III):

Exemplary preferred compounds according to formula (III) include the following: 14, 15, 20, 27, 32, 33, 36, 42, 45, 49, 55, 70, 75, 79, 80, 81, 82, 83, 84, and 86.

In another preferred embodiment, the compounds of the invention are compounds having the structural formula (IV):

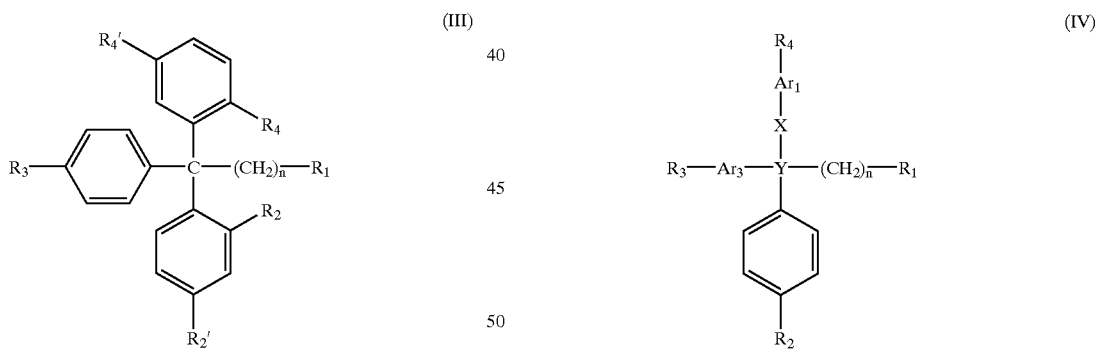

wherein:
n is 0, 1, 2, 3 or 4;
$R_1$ is —H, —OR, —SR, —CN, —C(O)R, —C(O)OR, —C(O)NR$_2$, —CH[C(O)R]$_2$ or —CH[C(O)OR]$_2$;
$R_2$ is —F, —Cl, —Br, —I, —OR, —SR, —C(O)R or —C(O)NR$_2$;
$R_{2'}$ is —H or —NO$_2$;
$R_3$ is —H, (C$_1$–C$_6$)alkyl, (C$_1$–C$_6$)alkenyl, (C$_1$–C$_6$) alkynyl, —OR or —SR;
$R_4$ is —H or —NR$_2$;
$R_{4'}$ is —H, —F, —Cl, —Br or —I; and
each R is independently selected from the group consisting of —H, (C$_1$–C$_6$)alkyl, (C$_1$–C$_6$)alkenyl, (C$_1$–C$_6$) alkynyl or (C$_1$–C$_6$)alkoxy.

wherein:
X is absent or —C≡C—;
Y is C, P, Si or Ge;
n is 0, 1, 2, 3 or 4;
Ar$_1$ is phenyl, substituted phenyl, cycloalkyl or heteroarylium other than imidazolium, nitroimidazolium or triazolium;
Ar$_3$ is phenyl, naphthyl, piperidyl or cyclohexyl;
$R_1$ is —R, —OR, —SR, —CN, —NR$_2$, —ONR$_2$, —C(O) R, —C(O)OR, —C(O)NR$_2$, —CH[C(O)R]$_2$, —CH[C (O)OR]$_2$, (C$_1$C$_6$)alkyl, (C$_1$–C$_6$)alkenyl, (C$_1$–C$_6$) alkynyl, cyclopenta-2,4-diene-1-ylidene or phenyl;
each of $R_2$, $R_3$ and $R_4$ is independently selected from the group consisting of —H, —F, —Cl, —Br, —I, —OR, —SR, —NR$_2$, —NO$_2$, —C(O)R, —C(O)OR, —C(O)NR$_2$, trihalomethyl, (C$_1$-C$_6$)alkyl, (C$_1$-C$_6$)alkenyl, (C$_1$-C$_6$)alkynyl and phenyl;

each R is independently selected from the group consisting of —H, halo, (C$_1$-C$_6$)alkyl, substituted (C$_1$-C$_6$)alkyl, (C$_1$-C$_6$)alkenyl, substituted (C$_1$C$_6$)alkenyl, (C$_1$-C$_6$)alkynyl, substituted (C$_1$-C$_6$)alkynyl and (C$_1$-C$_6$)alkoxy;

the alkyl, alkenyl or alkynyl substituents are each independently selected from the group consisting of aryl, —C(O)OR, pyrrolidinyl, butyrolactonyl, —F, —Cl, —Br, —I and —CN; and the phenyl substituents are each independently —R.

Exemplary preferred compounds according to formula (IV) include the following: 7, 10, 12, 13, 16, 18, 19, 21, 22, 23, 24, 26, 28, 29, 30, 31, 34, 35, 37, 38, 40, 41, 43, 44, 46, 47, 48, 50, 51, 52, 53, 54, 56, 58, 59, 60, 61, 62, 64, 65, 67, 68, 69, 71, 72, 73, 78, 87, 88, 89 and 90.

In another preferred embodiment, the aromatic compounds of the invention are compounds having the formula (V):

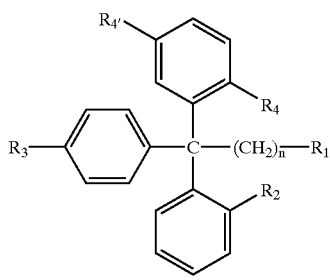

(V)

or pharmaceutically acceptable salts or hydrates thereof, wherein:

n is 0, 1, 2, 3 or 4;

R$_1$ is —H, —OR, —SR, —CN, —C(O)R, —C(S)R, —C(O)OR, —C(S)OR, —C(O)SR, —C(S)SR, —C(O)NR$_2$, —C(S)NR$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$;

R$_2$ is —F, —Cl, —Br or —I;

R$_3$ is —R, —OR or —SR;

R$_4$ is —H or —NR$_2$;

R$_{4'}$ is —H, —F, —Cl, —Br or —I; and each R is independently selected from the group consisting of —H, (C$_1$-C$_6$)alkyl, (C$_1$-C$_6$)alkenyl, (C$_1$-C$_6$)alkynyl and (C$_1$-C$_6$)alkoxy.

In another preferred embodiment, the compounds of the invention are those of formula (V), with the provisos that (i) when n is 0 and R$_1$ is —H or —OH, R$_3$ is other than —H; and (ii) when n is 0 and R$_1$ is —H, R$_3$ is other than —OH.

In another preferred embodiment, the compounds of the invention are those of formula (V), with the proviso that when n is 0 and R$_1$ is —C(O)NH$_2$, R$_2$ is other than -F.

Representative compounds according to formula (A) include Compounds 14, 15, 32, 33, 36, 55, 70, 75, 79, 80, 81, 82, 83, 84 and 86.

In another preferred embodiment, the aromatic compounds of the invention are compounds having the formula (VI):

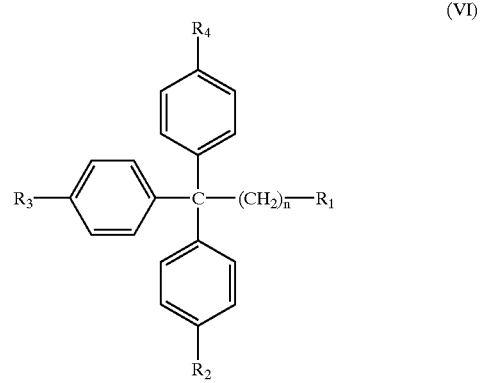

(VI)

or pharmaceutically acceptable salts or hydrates thereof, wherein:

n is 0, 1, 2, 3 or 4;

R$_1$ is —NR$_2$, —C(O)R, —C(S)R, —C(O)NR'$_2$ or —C(S)NR'$_2$;

R$_2$ is —F, —Cl, —Br or —I;

R$_3$ is —F, —Cl, —Br or —I;

R$_4$ is —F, —Cl, —Br or —I;

each R is independently selected from the group consisting of —H, (C$_1$-C$_6$)alkyl, (C$_1$-C$_6$)alkenyl, (C$_1$-C$_6$)alkynyl and (C$_1$-C$_6$)alkoxy; and each R' is independently selected from the group consisting of —H, (C$_1$-C$_6$)alkyl, (C$_1$-C$_6$)alkenyl, (C$_1$-C$_6$)alkynyl and (C$_1$-C$_6$)alkoxy.

Representative preferred compounds according to formula (VI) include Compounds 30, 40, 41 and 65.

In another preferred embodiment, the compounds of the invention are compounds having the formula (VII):

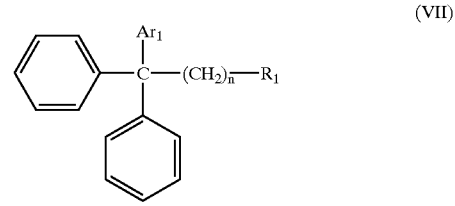

(VII)

or pharmaceutically acceptable salts or hydrates thereof, wherein:

n is 0, 1, 2, 3 or 4;

Ar$_1$ is phenyl or cyclohexyl;

R$_1$ is —NR$_2$, —CH[C(O)OR]$_2$, —CH[C(S)OR]$_2$, —CH[C(O)SR]$_2$, —CH[C(S)SR]$_2$, —C(O)NR$_2$ or —C(S)NR$_2$; and each R is independently selected from the group consisting of —H, (C$_1$-C$_6$)alkyl, (C$_1$-C$_6$)alkenyl, (C$_1$-C$_6$)alkynyl and (C$_1$-C$_6$)alkoxy.

In another preferred embodiment, the compounds of the invention are those of formula (VII), with the proviso that when R$_1$ is —NH$_2$ or —C(O)NH$_2$, n is 1, 2 or 3.

Representative preferred compounds according to formula (VII) include compounds 18, 29, 31, 56 and 78.

The aromatic compounds of the invention are commercially available compounds, are derived from commercially available compounds or are synthesized de novo using routine chemical synthetic procedures known to those of ordinary skill in the art. For instance, the compounds described herein may be prepared by any processes known to be applicable to the preparation of chemical compounds. Suitable processes are well known in the art. Preferred processes have been described in publications such as PCT Published Patent Application WO 97/34589. Necessary starting materials may be obtained commercially or by standard procedures of organic chemistry.

Moreover, many of the compounds of formula (I) are commercially available. For example, compound numbers 1, 2, 3, 4, 5, 6, 7, 8, 9, 10, 11, 12, 19, 20, 21, 23, 24, 25, 26, 28, 34, 37, 38, 39, 42, 43, 44, 45, 46, 47, 48, 49, 50, 51, 52, 54, 57, 59, 60, 61, 62, 66, 67, 69, 71, 72, 73, 76, 77 and 87 are commercially available.

In addition to the commercially available compounds many other aromatic compounds of formula (I) have been previously described in PCT Published Patent Application WO 97/34589 and other sources. For instance Compound 13 (U.S. Pat. No. 4,006,023); Compound 25 (WO 96/36631); Compound 26 (Fan et al., 1983, *Yiyao Gongye* 9:2–4); Compound 60 (Ethridge et al., 1990, *J. Production Agriculture* 3(2):246–252); Compound 76 (CAS No. 18740-94-8); Compound 77 (Ferguson et al., 1992, *Acta Crystallogr., Sect. C: Cryst. Struct. Commun.* C48(7):1228–1231); Compound 90 (1957, *Comptes. Rendus.* 245(1):73–75), 1,1-diphenyl-1-(2-hydroxynaphthyl)-methanol (Lewis et al., 1980, *J. Am. Chem. Soc.* 102(14):4659–4664; CA 083:018922); 1,1-diphenyl-1-(pyrid-2-yl)-methanol, 1-(4-chlorophenyl)-1-phenyl-1-(pyrid-2-yl)-methanol, 1-(4-methoxyphenyl)-1-phenyl-1-(pyrid-3-yl)-methanol and 1,1-di-(4-methoxyphenyl)-1-(pyrid-3-yl)-methanol (Illes et al., 1988, *Acta Phytopathologica et Entomologia Hungarica* 23:243–255); 1,1,1-triphenyl-1-aminomethane and 1,1-diphenyl-1-(N-pyridyl)-methane (Matsuura et al., 1991, *Biochem. Pharmacol.* 41:1949–1956); 4,4'-dimethoxytrityl chloride, pixyl chloride, di-o-anisyl-1-naphthyl-methyl chloride and p-anisyl-1-naphthyl-methyl chloride (Gait, 1984, *Oligonucleotide Synthesis: A Practical Approach*, IRL Press, Oxford) have all been described. Additionally, Compounds 6, 17 and 85 which are metabolites of Clotrimazole have been described (Duhm et al., 1974, *Postgraduate Medical Journal July Suppl*.:13–16).

The active compounds of the invention exhibit a pharmacological activity, the inhibition of $Cl^-$ secretion from intestinal cells. Any compound encompassed by formula (I) which exhibits this pharmacological activity is considered to be within the scope of the present invention. This activity may be assessed using standard techniques known in the art such as the assays described below with respect to effective amounts or in the Examples section.

The chemical formulae referred to herein may exhibit the phenomena of tautomerism or conformational isomerism. As the formulae drawings within this specification can represent only one of the possible tautomeric or conformational isomeric forms, it should be understood that the invention encompasses any tautomeric or conformational isomeric forms which exhibit biological or pharmacological activity as described herein.

The compounds of the invention may be in the form of free acids, free bases or pharmaceutically effective salts thereof. Such salts can be readily prepared by treating a compound with an appropriate acid. Such acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propandioic acid, butandioic acid, etc. Conversely, the salt can be converted into the free base form by treatment with alkali.

In addition to the above-described compounds and their pharmaceutically acceptable salts, the invention may employ, where applicable, solvated as well as unsolvated forms of the compounds (e.g. hydrated forms).

Diarrhea, as used herein, indicates a medical syndrome which is characterized by the symptoms of diarrhea or scours. In general, diarrhea is a disorder resulting in a secretory imbalance. For purposes of this patent application diarrhea is divided into three categories based on the underlying mechanism: exudative, decreased absorption, and secretory and the term diarrhea as used herein encompasses each of these categories. Exudative diarrheas result from inflammatory processes leading to impaired colonic absorption, and outpouring of cells and colloid caused by such disorders as ulcerative colitis, shigellosis, and amebiasis. Disorders of decreased absorption include osmotic, anatomic derangement, and motility disorders. Osmotic diarrhea can occur as a result of digestive abnormalities such as lactose intolerance. Anatomic derangement results in a decreased absorption surface caused by such procedures as subtotal colectomy and gastrocolic fistula. Motility disorders result from decreased contact time resulting from such diseases as hyperthyroidism and irritable bowel syndrome. Secretory diarrhea is characterized by the hypersecretion of fluid and electrolytes from the cells of the intestinal wall.

In classical form, the hypersecretion is due to changes which are independent of the permeability, absorptive capacity and exogenously generated osmotic gradients within the intestine. As discussed above, however, all forms of diarrhea may actually manifest a secretory component.

The methods and products of the invention are particularly useful in treating diarrhea which is secretory. However, the methods and products of the invention may also be used in combination with other treatment methods which are known in the art to treat diarrhea caused by decreased absorption or inflammation. The compounds of the invention are involved in regulating $Cl^-$ secretion and can function alone or when used in combination with other treatment methods to decrease net fluid secretion even when this is due primarily to abnormalities in absorption or inflammation.

The methods and products of the invention are useful in preventing diarrhea and scours in subjects at risk of developing these disorders. Subjects at risk of developing diarrhea and scours are those subjects which have a high likelihood of exposure to the bacterial and viral microorganisms which cause these symptoms. For example, approximately ⅓ of travelers to developing countries will develop diarrhea; infection with rotavirus is one of the leading causes of death in infants in developing countries; patients with HIV have a greater than 50% chance of developing diarrhea, and many newborn calves and pigs develop scours. Patients with inflammatory bowel disease develop recurrent diarrhea.

The methods and products of the invention are also useful in treating subjects who already exhibit the symptoms of diarrhea and scours. Once a subject has been exposed to a microorganism causing the symptoms, the subject may be treated with the methods and products of the present invention in order to reduce the symptoms. The symptoms of diarrhea include bowel irregularity, fecal fluid rich in sodium or potassium, fluid feces, dehydration, fever, loss of body weight, headache, anorexia, vomiting, malaise and myalgia. The symptoms of scours include a loss of body weight or failure to grow, dehydration, malodorous feces, fluid feces, feces containing pieces of partially digested milk or semi-solid material, and feces of a yellow-white or gray color.

One product of the invention is a veterinary preparation of an aromatic compound of the invention, used alone or combined with an anti-scours agent. An anti-scours agent is a composition which is known to be useful in preventing or inhibiting the symptoms of scours. Known compositions include, for example, colostral extracts, such as those described in U.S. Pat. No. 4,377,569 and Canadian patent no. 1,175,352 and widely commercially available (e.g. Soluble Colostrum Powder, by VedCo, Inc., St. Joseph Mo.; Colostrum Bolus II, by RX Veterinary Products, Kansas City Mo., etc.); an immunological preparation of colostrum isolated from milk-producing mammals which may have been immunized against certain diarrheal causing microorganisms, such as those described in U.S. Pat. No. 4,834,974, Australian patent no. 39340/89, Australian patent no. 52547/90, and German patent no. 1,560,344; microorganism specific immunological preparations, including microorganism specific hybridoma-derived monoclonal antibodies such as those described in Sherman et al., *Infection and Immunity*, V. 42 (2), P. 653–658 (1983) and a bovine immunoglobulin fraction prepared from bovine plasma or clear bovine serum such as the fraction described in U.S. Pat. No. 3,984,539; oral rehydration fluids and/or replacement electrolyte compositions which are widely commercially available in the form of dry compositions or liquid solutions prepared for oral or intravenous administration (e.g. Electrolyte H, by Agri-Pet Inc., Aubrey Tex.; Electrolyte Powder 8x, by Phoenix Pharmaceutical Inc, St. Joseph Mo.; Electrolyte Solution Rx, by Lextron Inc., Greeley Colo., ProLabs LTD, St. Joseph Mo., and VetTek Inc., Blue Springs Mo.; Calf Rehydrate, by Durvet Inc., Blue Springs Mo., etc.) and antibiotic compositions which are commercially available (e.g. BIOSOL® Liquid, by The UpJohn Company Animal Health Division, Kalamazoo Mich.; AMOXIBOL®, by SmithKline-Beecham Animal Health, Exton Pa.; 5-WAY CALF SCOUR BOLUS™, by Agri Laboratories LTD, St. Joseph Mo.; 1-A-DAY CALF SCOUR BOLUS, by A.H.A.; GARACIN® PIG PUMP, by Schering-Plough Animal Health Corporation, Kenilworth N.J., etc.).

In one embodiment, the veterinary preparation is a dry preparation of the aromatic compound of the invention and an antiscours agent. The dry preparation may be administered directly or may be hydrated and/or diluted in a liquid solution prior to administration. In another embodiment, the veterinary preparation is a liquid solution of the compound of the invention and an anti-scours agent.

Another product of the invention is a pharmaceutical preparation of an aromatic compound of the invention and an anti-diarrheal agent. An anti-diarrheal agent includes, for example, an immunoglobulin preparation from bovine colostrum; lomotil; an intravenous or oral rehydration fluid; a dry rehydration composition salt; an electrolyte replacement composition (in dry or liquid form); an oral or intravenous sugar-electrolyte solution or dry composition; an antibiotic such as tetracycline, trirmethoprim or sulfamethoxazole; a quinolone drug such as norfloxacin or ciprofloxacin, bismuth subsalicylate, diphenoxylate; and loperamide.

In one embodiment the pharmaceutical preparation is a dry preparation of the aromatic compound of the invention and an anti-diarrheal agent. The dry preparation may be administered directly or may be hydrated and/or diluted in a liquid solution prior to administration. In another embodiment the pharmaceutical preparation is a liquid solution of the aromatic compound of the invention and an anti-diarrheal agent.

A subject as used herein, means humans, primates, horses, cows, sheep, pigs, goats, cats and dogs.

The time of administration of the aromatic compounds useful according to the invention varies depending upon the purpose of the administration. When the compounds of the invention are administered in order to prevent the development of diarrhea in subjects traveling to areas with high risk of exposure to infectious agent or subjects otherwise exposed to diarrhea causing agents, the compounds should be administered at about the time that the subject is exposed to the risk or the high risk area. When the compounds are administered to subjects in order to prevent the development of scours, the veterinary preparation should be administered within the first 12 hours after birth, and preferably within the first 4 hours after birth. When the compounds of the invention are used to treat subjects having symptoms of diarrhea or scours, the compounds may be administered at any point while the subject is experiencing symptoms, and preferably as soon as the symptoms develop.

When administered, the formulations of the invention are applied in pharmaceutically acceptable amounts and in pharmaceutically acceptable compositions. Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulfuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V).

Suitable preservatives include benzalkonium chloride (0.003–0.03% W/V); chlorobutanol (0.3–0.9% W/V); parabens (0.01–0.25% W/V) and thimerosal (0.004–0.02% W/V).

The active compounds of the present invention may be pharmaceutical compositions having a therapeutically effective amount of an aromatic compound of the general formula provided above in combination with an anti-diarrheal agent, optionally included in a pharmaceutically-acceptable carrier. The active compounds of the present invention also may be veterinary compositions having a therapeutically effective amount of an aromatic compound of the general formula provided above in combination with an anti-scours agent, optionally included in a pharmaceutically-acceptable carrier. The term "pharmaceutically-acceptable carrier" as used herein means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the compound of the present invention, with the anti-diarrheal or anti-scours agents, and with each other, in a manner such that there is no interaction which would substantially impair the desired pharmaceutical efficacy.

A common administration vehicle (e.g., pill, tablet, bolus, powder or solution for dilution, pig pump, implant, injectable solution, etc.) would contain both the compounds useful in this invention and the anti-diarrheal or anti-scours agent. Thus, the present invention provides pharmaceutical or veterinary compositions, for medical or veterinary use, which comprise the active compounds of the invention together with one or more pharmaceutically acceptable carriers thereof and other therapeutic ingredients.

The formulations of the invention are administered in effective amounts. An effective amount is one sufficient to inhibit the $Cl^-$ secretion of intestinal epithelial cells, thereby effectively decreasing the secretory response, thereby resulting in a decrease in diarrhea or scours and/or the symptoms thereof. Effective amounts will depend, of course, on the particular condition being treated; the severity of the condition; individual patient parameters including age, physical condition, size and weight; concurrent treatment; frequency of treatment; and the mode of administration. These factors are well known to those of ordinary skill in the art and can be addressed with no more than routine experimentation.

An effective amount for an individual compound may be assessed using any method known in the art which reliably determines the amount of $Cl^-$ secretion from intestinal cells. A compound may be subject to a series of standard assays or screens to determine its pharmacological activity and effective amounts.

In general, the active compounds of the invention are those which induce at least about 25% inhibition of the $Cl^-$ secretion, as measured using in vitro assays that are commonly known in the art (see, e.g., Example 4). Alternatively, or in addition, the active compounds of the invention generally will have an $IC_{50}$ (concentration of compound that yields 50% inhibition) for inhibition of the $Cl^-$ secretion of less than about 10 $\mu$M as measured using in vitro assays.

It is preferred generally that a maximum dose be used, that is, the highest safe dose according to sound medical judgment, particularly if acute diarrhea or scours are the dominant clinical manifestation. Dosage may be adjusted appropriately to achieve desired drug plasma levels. Generally, daily oral doses of active compounds will be from about 0.01 milligrams/kg per day to 1000 milligrams/kg per day. It is expected that oral doses in the range of 50 to 500 milligrams/kg, in one or several administrations per day, will yield the desired results. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

A variety of administration routes are available. The particular mode selected will depend of course, upon the particular drug selected, the severity of the diarrhea or scours being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis. They could, however, be preferred in emergency situations. Oral administration will be preferred for prophylactic treatment because of the convenience to the subject as well as the dosing schedule.

The compositions may conveniently be presented in unit dosage form and may be prepared by any of the methods well known in the art of pharmacy. All methods include the step of bringing the active compounds into association with a carrier which constitutes one or more accessory ingredients. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachets, tablets, or lozenges, each containing a predetermined amount of the active compound. Other compositions include suspensions in aqueous liquors or non-aqueous liquids such as a syrup, an elixir, or an emulsion. Active ingredients administered orally may be in any form suitable for oral administration, e.g., a pill, tablet, bolus, drinking solution, liquid or powder composition to be diluted or mixed with food, pig pump, etc.

Compositions suitable for parenteral administration conveniently comprise a sterile aqueous preparation of the active compound, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di- and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Use of a long-term sustained release implant may be particularly suitable for treatment of diarrhea in immunodeficient patients, who need continuous administration of the compositions of the invention. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

The following examples depict tests that are employed to determine the effects on Cl⁻ secretion. Clotrimazole, which is outside of the scope of the present claims is used to exemplify how the compounds of the present invention are tested. The compounds of the present invention are structurally distinct from the structure of clotrimazole. Nevertheless, the compounds of the present invention act as chloride secretion in the same manner as clotrimazole and, therefore, are useful in the methods and products of the present invention.

EXAMPLES

Example 1

Clotrimazole Inhibits Water and Electrolyte Secretion in Intestinal Epithelial Cells The biochemical basis of secretory diarrhea involves intestinal Cl⁻ secretion in intestinal crypt cells. Under normal conditions, Cl⁻ ions are maintained within intestinal crypt cells at levels above their electrochemical potential by primarily and secondarily active transport mechanisms such as the Na/K ATPase pumps and Na/K/2Cl cotransporters. Cl⁻ is transported into the lumen from the intestinal crypt cells through apical Cl⁻ channels. Intracellular levels of $K^+$, cAMP, cGMP, and $Ca^{++}$ are all involved in regulating the secretory response.

T84 cells were used to determine whether clotrimazole regulates Cl⁻ secretion in intestinal crypt cells. T84 cells form confluent monolayers of columnar epithelia that exhibit high transepithelial resistances, polarized apical and basilateral membranes, and cAMP and $Ca^{++}$ regulated Cl⁻ secretory pathways analogous to those found in native intestine.

Methods

Growth of T84 cells: T84 cells obtained from ATCC were cultured and passaged in equal parts of dulbecco's modified eagle's medium (DMEM), 1 g/l D-glucose) and Hams F-12 nutrient mixture, supplemented with 5% newborn calf serum, 15 mM HEPES, 14 mM Na $HCO_3$, 40 mg/l penicillin, 8 mg/l ampicillin, 0.90 mg/l streptomycin. Cells were seeded at confluent density onto 0.33 $cm^2$ or 5 $cm^2$ Transwell inserts (Costar, Cambridge, Mass.) coated with dilute rat collagen solution as previously described (Lencer et al., *J. Clin. Invest.*, 92: 2941–2951 (1993); Lencer et al., *J. Cell Biol.* 117: 1197–1209 (1992). Transepithelial resistances attain stable levels (>1000 Ohms·$cm^2$) after 7 days. The development of high transepithelial resistances correlated with the formation of confluent monolayers with well-developed tight junctions as assessed by morphological analysis, and with the ability of monolayers to secrete Cl⁻ (Madara et al., *Gastro.* 92: 1133–1145 (1987).

Electrophysiology (mesurement of elctrogenic Cl⁻ secretion): Confluent monolayers were transferred to Hanks Buffered Salt Solution (HBSS) containing 0.185 g/l $CaCl_2$, 0.098 g/l $MgSO_4$, 0.4 g/l KCl, 0.06 g/l $KH_2PO_4$, 8 NaCl, 0.048 g/l $Na_2HPO_4$, 1 g/l glucase, and 10 nm HEPES, pH 7.4. Serosal and mucosal reservoirs were interfaced with Calomel and Ag—Ag Cl electrodes via 5% agar bridges made with Ringer's buffer. Transepithelial resistance was measured using a dual voltage clamp device to apply 25 or 50 μA current pulses. Short circuit current (ISC) was calculated using Ohms law as previously described (Lencer et al., *J. Clin. Invest.* 92: 2941–2951 (1993); Lencer et al. *J. Cell Biol.* 117: 1197–1209 (1992).

Results:

Clotrimazole reversibly inhibits Cl⁻ secretion elicited by $Ca^{++}$- or cAMP-dependant agonists in T84 cells: Previous studies have shown that Cl⁻ secretion in T84 cells is controlled by $K^+$ efflux pathways which are biophysically and pharmacologically distinct from one another. One pathway participates in the secretory response to cAMP-dependent agonists and displays sensitivity to $Ba^{++}$ salts (McRoberts, et al., *J. Biol. Chem.* 260: 14163–14172 (1985); Reenstra, *Am J. Physiol.* 264: C161–168 (1993)). The other mediates the response to $Ca^{++}$-dependent agonists, and is $Ba^{++}$-insensitive. Several pathway specific agonists of $K^+$ channels are useful for determining whether a particular compound is functioning through a cAMP or $Ca^{++}$ specific pathway. For instance, vasoactive intestinal peptide (VIP) and cholera toxin are cAMP mediated agonists of the $K^+$ channel, whereas, carbachol is a $Ca^{++}$-dependent agonist of the $Ca^{++}$ regulated $K^+$ channels. The pathway by which a particular inhibitor of Cl⁻ secretion in T84 cells is functioning may be identified by measuring the ability of the inhibitor to modify transepithelial resistances in T84 cells which have been treated with VIP or carbachol to stimulate Cl⁻ secretion.

T84 cells were grown as described above and Cl⁻ secretion was stimulated by the addition to the media of either carbachol (100 mM) or VIP (5 nM). The cells were then treated with BaCl (3 mM), charybdotoxin (100 nM), or clotrimazole (33 mM). The short circuit current (ISC) was determined for the various inhibitor treatments as a percentage of the control in the absence of inhibitor (FIG. 1). BaCl strongly inhibited the secretory response to the cAMP mediated agonist IP, but had no apparent affect on the secretory response elicited by the $Ca^{++}$-dependent agonist carbachol. In contrast, the scorpion venom Charybdotoxin strongly inhibited the secretory response elicited by carbachol, but had minimal affects on Cl⁻ secretion elicited by VIP. However, clotrimazole inhibited the Cl⁻ secretory responses to both agonists. Inhibition of Cl— secretion by clotrimazole was fully reversible (96±2%, n=4) after 60 min recovery in the presence of 0.01 mg/ml bovine serum albumin.

To examine possible effects of clotrimazole on the synergy between cAMP and $Ca^{++}$-mediated agonists, monolayers, initially stimulated with VIP were allowed to reach steady-state levels of secretion and then additionally exposed to carbachol (100 μM). Clotrimazole was slightly more effective in inhibiting the secretory response to carbachol than to cAMP with IC50 values of 3 and 8 μM, respectively. When the effects of clotrimazole on cAMP- and $Ca^{++}$-dependent secretory pathways were examined on the same monolayers, inhibition of the synergistic response to VIP plus carbachol was found to parallel the inhibition of secretion promoted by $Ca^{++}$ agonists alone. In low doses (=$10^{-7}$ or less), clotrimazole potentiated slightly (by 5–10%) the CI-secretory responses to either agonist. clotrimazole inhibited effectively the secretory response to cholera toxin (20 nM, a cAMP-dependent agonist) and *E. Coli* heat-stabile toxin (100 nm, a cGMP-agonist) (IC50 values of 10 μM and 15 μM, respectively).

The effect of clotrimazole on $K^+$ conductances was also examined by isotopic flux studies using $^{86}$RB. T84 cells were grown in the presence of a cAMP agonist, VIP, or a $Ca^{++}$ mediated agonist (Thapsigargin). Clotrimazole was added and $^{86}$RB efflux was measured. Clotrimazole significantly inhibited baseline and $Ca^{++}$ stimulated $^{86}$RB efflux in the presence of both cAMP and $Ca^{++}$ mediated agonists compared to those cells which were not treated with clotrimazole.

Other aromatic compounds of the invention were found to inhibit chloride secretion. Although clotrimazole was the most potent inhibitor tested of cAMP and $Ca^{++}$ elicited Cl— secretion, ketoconazole, econazole, miconazole, and 2-chlorophenyl-bis-phenyl methanol also were effective at inhibiting chloride secretion.

Taken together, these studies indicate that clotrimazole inhibits $Cl^-$ secretion elicited by cAMP or $Ca^{++}$ mediated $K^+$ channels in T84 cells.

Example 2

Clotrimazole Acts at Distal Steps in the cAMP and $Ca^{++}$-dependent Signal Transduction Pathways To determine the site of clotrimazole action, the effects of clotrimazole pretreatment were examined on monolayers stimulated with agonists that initiate $Cl^-$ secretion at sequential steps in the cAMP signalling cascade. T84 monolayers were preincubated in HBSS in the presence or absence of clotrimazole (33 $\mu$M) and then stimulated with either 5 $\mu$M VIP (which activates adenylate cyclase through heterotrimeric GTPase-linked cell surface receptors), 10 $\mu$M forskolin (which activates adenylate cyclase directly), or 3 mM 8Br-cAMP (a direct stimulator of protein kinase A). Clotrimazole inhibited the secretory response to each of these agonists. These data provide evidence that clotrimazole acts at a step distal to the activation of Protein Kinase A.

$Ca^{++}$-dependent intracellular signaling in T84 and other non-exciteable cells involves recruitment of inositol trisphosphate (IP3)-dependent intracellular $Ca^{++}$ stores (Halm and Frizzell, *Textbook of secretory Diarrhea*, Raven Press, 47–58 (1990); Mandel et al., *J. Biol. Chem.* 267: 704–712 (1986); Halm et al., *Am. J. Physiol. (Cell Physiol.* 23) 254:C505–C511 (1988)), and subsequent activation of plasma membrane $Ca^{++}$ influx pathways (Barrett, *Am. J. Physiol. (Cell Physiol.* 34): C859–C868 (1993)). Downstream events may be mediated by $[Ca^{++}]i$, IP3, diacylglycerol, or as yet unidentified diffusable factors (Putney and Bird, *Cell* 75:199–201 (1993)). To examine the site of clotrimazole action alone, this signalling, cascade, T84 monolayers pretreated in the presence or absence of clotrimazole (33 $\mu$M) were stimulated with the $Ca^{++}$-dependent agonists carbachol (100 $\mu$M which elicits both $Ca^{++}$ and $IP_3$ signals), thapsigargin (5 $\mu$M, which elevates cytoplasmic $Ca^{++}$ via inhibition of ER $Ca^{++}$-ATPase) (Vandorpe et al., *Biophys. J.* 66:46–58 (1994)), or the $Ca^{++}$ ionophore ionomycin (10 $\mu$m). Clotrimazole inhibited strongly the Cl-secretory response to each to these reagents. These data suggest that clotrimazole acts at steps in the secretory response distal to the release of intracellular $Ca^{++}$ stores.

Example 3

Clotrimazole Does Not Affect Apical Membrane Anion Conductance or Basolateral NaK2Cl Cotransporters Methods $^{125}I$ Efflux Studies Confluent monolayers on 5 $cm^2$ Transwell inserts were used 10–14 days after plating. $^{125}I$ was measured as an indicator of apical Cl—, channel and basolateral $K^+$ channel activity as previously described (Venglarik, et al, *Am. J. Physiol. (Cell Physiol.* 28):C358–C364 (1990). Monolayers were preincubated at 37° C. with 4 $\mu$Ci/ml $^{125}I$ in HBSS for 90 minutes, with 33 $\mu$M clotrimazole absent or present during the final 30 minutes of this 90 min preincubation period. Clotrimazole pretreatment did not alter $^{125}I$ loading of the cells. After washing twice in fresh HBSS, 0.5 ml samples were obtained every two min from the apical reservoir and replaced with fresh HBSS. After four baseline samples were obtained, the cells were treated (at t=8 minutes) with vasoactive intestinal peptide (VIP, 5 $\mu$nM) or thapsigargin (5 $\mu$M) to stimulate Cl— secretion, and an additional 15 timed samples were obtained. Finally, the cell monolayer was rinsed, cut with its support from the polystyrene ring, and the residual cell-associated radioactivity was determined. Monolayers were maintained at 37° C. in room air throughout the study. $^{125}I$ was counted by gamma counting and normalized to percent total uptake as previously described (Venglarik, et al, *Am. J. Physiol. (Cell Physiol.* 28):C358–C364 (1990).

$^{86}Rb$ Uptake Studies

Confluent monolayers on 5 $cm^2$ Transwell inserts were incubated for 30 minutes in HBSS at 37° C. A group of control and CLT treated (33 $\mu$M, for 30 min) monolayers were treated with bumetanide (10 $\mu$M for 12 min). All monolayers were then treated with VIP (5 nM and shifted to HBSS containing 1 $\mu$Ci/ml $^{86}Rb$ for 3 minutes at 37° C. Rb uptake was terminated by washing the inserts in an ice-cold solution containing 100 mM $MgCl_2$, and 10 mM TRIS-CL, pH 7.4. Monolayers were cut from their inserts, placed into scintillation vials, and counted usina standard methods.

Results

Studies were conducted to determine whether the inhibition of electrogenic Cl— secretion might occur by blockade of apical membrane Cl-channels, or blockade of basolaterally situated NaK2Cl cotransporters. To determine if clotrimazole affected ion conductance through apical membrane Cl-channels, we examined the time course of $^{125}I$ efflux from T84 monolayers pretreated in the presence or absence of clotrimazole (Venglarik, et al, *Am. J. Physiol. (Cell Physiol.* 28):C358–C364 (1990). Clotrimazole had little or no effect on the time course of $^{125}I$ efflux from monolayers treated with VIP. Rate constants for 125I efflux from monolayers treated or not treated with clotrimazole were indistin!-L:,.shable (0.0637 vs.0.0645% uptake/minute, n=2 in duplicate). Clotrimazole had similar lack of effect on 125I efflux stimulated by thapsigargin.

We next tested the effect of clotrimazole on basolateral NaK2CI cotransporters, as assessed by bumetanide-sensitive $^{86}Rb$ uptake (Matthews et al., *J. Biol. Chem.* 269:15703–15709 (1994)). Clotrimazole treatment reduced the total amount of $^{86}Rb$ uptake by 53.6±15.8% (mean±SEM. n=6), but had no effect on the fractional component that was bumetanide-sensitive (88±3.2 vs 75.2±12.7% total uptake, mean±SEM). Taken together, these data strongly suggest that clotrimazole does not affect CI— secretion in T84 cells via inhibition of either apical membrane $Cl^-$ channels or basolateral membrane NaK2Cl cotransporters.

Example 4

Clotrimazole Inhibits Chloride Secretion by Inhibiting K+ Efflux Through Basolateral K+ Channels in T84 Cells Methods 1. Clotrimazole Inhibits Chloride Secretion by Blockade of $K^+$ Transport Through Both Ba++-sensitive and Charybdotoxin-sensitive Channels $^{86}Rb$ Efflux Studies Confluent monolayers on 5 $cm^2$ Transwell inserts were used 10–14 days after plating. $^{86}Rb$ flux was measured as an indicator of apical Cl—, channel and basolateral K+ channel activity as previously described (Venglarik, et al, *Am. J. Physiol. (Cell Physiol.* 28):C358–C364 (1990). Monolayers were preincubated at 37° C. with 4 µCi/ml $^{86}$Rb in HBSS for 90 minutes, with 33 µM clotrimazole absent or present during the final 30 minutes of this 90 min preincubation period. clotrimazole pretreatment did not alter $^{86}$Rb loading of the cells. One ml samples were obtained and replaced from the basolateral reservoir. After four baseline samples were obtained, the cells were treated (at t=8 minutes) with vasoactive intestinal peptide (VIP, 5 µmM) or thapsigargin (5 µM) to stimulate Cl$^-$ secretion, and an additional 15 timed samples were obtained. Finally, the cell monolayer was rinsed, cut with its support from the polystyrene ring, and the residual cell-associated radioactivity was determined. Monolayers were maintained at 37° C. in room air throughout the study. $^{86}$Rb was counted by scintillation counting and normalized to percent total uptake as previously described (Venglarik, et al, *Am. J. Physiol. (Cell Physiol.* 28):C358–C364 (1990).

Results

K+ channel activity was estimated by measurement of $^{86}$Rb efflux. Clotrimazole was found to significantly inhibit the rate of $^{86}$Rb efflux after treatment with the cAMP agonist VIP (5 µM). The rate constant for VIP-stimulated $^{86}$Rb efflux was reduced by 87% in monolayers treated with clotrimazole (0.0062 vs. 0.0465% uptake/minute, n=2 in triplicate). clotrimazole inhibited to a similar degree $^{86}$Rb efflux from monolayers stimulated with thapsigargin (panel B, rate constants 0.011 vs. 0.048% uptake/minute, n=2), suggesting that clotrimazole can inhibit Cl— secretion by blockade of K+ transport through both Ba++-sensitive and charybdotoxin-sensitive channels.

2. Clotrimazole Inhibits Chloride Secretion Through Distinct cAMP and Ca$^{++}$ Sensitive Basolateral K$^+$ Channels Selective mebrane Permeabilization and Measurement of Potassium Conductance of the Basolateral Membrane. The basolateral potassium conductance was measured using the technique developed by Dawson and co-workers. A potassium gradient (mucosal to serosal) was first established across the monolayer using asymmetric mucosal and serosal buffers containing K$^+$ as the sole permeant ion. The addition of amphotericin B (20 µM) to the mucosal reservoir forms conductive pores in the apical membrane, and thus removes all resistance to transepithelial potassium movement across this membrane. Thus, under the conditions of the experiment, in which the monolayer is short circuited (i.e., voltage-clamped at zero potential) and the transepithehal potassium gradient is constant, the amphotericin-dependent Isc becomes a measure of the rate of the transepithelial potassium flux across basolateral membranes. Changes in short circuit current (Isc), then represent changes in basolateral K$^+$ conductances (gK). Isc and K$^+$ conductances were measured using calomel electrodes, 3M KCl-agar bridges, and a voltage clamp (University of Iowa, Iowa City). To generate a voltage-current channel relationships, currents were elicited by 1 sec test potentials from –80 to +80 in 10 mV increments in the asymmetrical high K$^+$ gluconate solution.

Calculation of Basolateral Membrane K$^+$ Permeability: Membrane Permeabilities were Calculated According to the Formula:

$$^PK=(cm/s)=^IK(mM/cm^2 \cdot s)/\Delta[K^+](mM/cm^3)$$

where $\Delta[K^+]$ is equal to the difference in K$^+$ concentration (135 mM) between the asymmetric apical and basolateral bathing solutions. Maximal Isc values were converted into K$^+$ fluxes by dividing by the Faraday constant F (96,500 coulombs/mol) as previously described (Huflejt et al., *J. Clin. Invest.* 93: 1900–1910 (1994)).

Results

Basolateral K+ transport was examined in T84 monolayers permeabilized apically by pretreatment with amphotericin B. Apical and basolateral buffers contained K+ as the sole permeant ion. All studies were performed with a 135 mM basolaterally directed K+ gradient. This method has been utilized previously to examine both Cl— and K+ transport in T84 cells and HT29-Cl.16E cells. Briefly, ion conductances in the luminal or basolateral membranes of confluent T84 cell monolayers can be assessed separately by selectively permeabilizing the apical or basolateral membrane using the ionophore amphotericin B. This artificially removes all electrical resistance to ion transport across the plasma membrane containing pores formed by amphotericin B. As a result, the intact contralateral plasma membrane becomes rate limiting for transepithelial ion transport. Agonist-dependent changes in ion conductances can be assessed directly either as transepithelial short circuit current (Isc) in the presence of established ion gradients, or as transepithelial conductance (G) in the presence of established transepithelial potentials.

K+ transport was measured at baseline and after the ordered additions of cAMP- and Ca$^{++}$-agonists. The initial permeabilization with amphotericin B was associated with 49±19% increase in conductance. Pores formed by amphotericin B display selectivity for monovalent cations. Ca$^{++}$ remained relatively impermeant as evidenced by the small steady state increase in Isc and $G_K$ caused by apical permeabilization with amphotericin B. Given this low baseline Isc 20 and $G_K$, both cAMP- and Ca$^{++}$-sensitive K$^+$ permeabilities (PK) were readily apparent after agonist stimulation. Treatment with the cAMP-agonist forskolin (10 µM) caused a brisk increase in K+ transport through apparently low-conductance pathway(s), as evidenced by symmetrical increases in Isc and G. Carbachol also increased K+ currents. The magnitude of the carbachol-induced IscK, however, was similar whether carbachol was added alone or after forskolin (111.7±7.4 vs. 180.7±15.7 µA/cm$^2$ respectively. Thus, there was no clear evidence of synergy between cAMP and Ca$^{++}$ mediated K+ pathways, as would be expected in an apically permeabilized cell system. Analagous to our previous findings in intact T84 monolayers, the forskolin-induced changes in Isc were sustained while the effect of carbachol was short-lived. Both $Isc_K$ and $G_K$ returned to baseline values within 5 min after addition of carbachol.

Formal current/voltage (I/V) relations were defined before and after agonist stimulation to confirm that both cAMP- and Ca$^{++}$-dependent currents were elicited at physiologic membrane potentials. Thapsigargin was used in place of carbacol as a Ca$^{++}$-agonist in these studies because the K+ transients elicited by thapsigargin achieve steady state conductances of much longer duration, as in intact monolayers. It was found that under conditions of basolaterally directed K+ gradients, both forskolin and thapsigar@ activate macroscopic outwardly rectified (mucosal to serosal) currents at positive transepithial voltages. Experimental I/V relations obtained after forskolin and thapsigargin stimulation displayed reversal potentials (−40 mV) that approximated the calculated Nemst-potential (−85 mV calculated as RT/zQo log $[Na]_{out}/[Na]_{in}$). These results are consistent with the activation of distinct cAMP- and Ca$^{++}$-sensitive basolateral membrane K+ conductances in conjunction with one or more nonspecific transepithelial ion shunts, possibly occurring through intercellular tight junctions or basolateral membrane "leaks."

To confirm that the observed changes in Isc and G represented K+ transport through K+ selective pathways, the effect of forskolin and carbachol on T84 monolayer conductances were examined using buffers containing $Na^+$ as the sole permeant cation. These studies were performed using an analogous 135 mM basolaterally directed cation (Nea) gradient. Increases in Isc and G were not detectable in the absence of K+. Thus, the increases in cation conductances induced by agonist stimulation are specific to K+ transport.

Two pharmacologically distinct K+ efflux pathways have been previously identified in intact T84 cells. One pathway participates in the secretary response to cAMP-dependent agonists and displays sensitivity to $Ba^{++}$ salts. The other K+ efflux pathway mediates the response to $Ca^{++}$-dependent agonists, and is $Ba^{++}$-insensitive. These findings were confirmed in the permeabolized cell model. The cAMP-sensitive $I_K$ (elicited by treatment with forskolin, 10 $\mu M$) was inhibited by greater than 70% by the addition of $BaCl_2$ (3 mM) to basolateral reservoirs. $Ba^{++}$, however, had no detectable effect on K+ transport induced by the subsequent addition of carbachol (100 $\mu M$) to the same monolayers. In contrast, when permeabilized monolayers were treated first with carbachol, the induced $Ca^{++}$ $I_K$ was inhibited by 50% by pretreatment with the scorpion venom charybdotoxin (100 nM). Charybdotoxin, however, had no detectable effect on K+ transport induced by the subsequent addition of forskolin. Thus in permeabilized cells, the differential sensitivity of K+ transport to inhibition by the K+ channel blockers $BaCl_2$ and charybdotoxin paralleled exactly the effect of these channel selective inhibitors on K+ transport in intact cells (measured indirectly as a $Cl^-$-current).

Taken together, these studies define the permeabilized T84 cell model, and provide strong evidence that under the defined conditions both Isc and G represent K+ transport through distinct cAMP- and $Ca^{++}$-sensitive basolateral K+ channels.

3. Clotrimazole and 2-Chlorophenyl-bs-phenyl Methanol, a Structurally Related Stable Metabolite, Inhibit K+ Transport Through Both cAMP- and $Ca^{++}$-Dependent K+ Channels We next tested the hypothesis that clotrimazole may inhibit directly basolateral membrane K+ channels in human intestinal T84 cells, as it does in the red cell. Clotrimazole significantly inhibited the time course of $K^+$ transport after treatment with the cAMP agonist forskolin (10 $\mu M$) and the $Ca^{++}$ agonist carbachol (100 $\mu M$). Formal IV relations taken at steady state after cAMP or $Ca^{++}$ stimulation confirm that clotrimazole affected both cAMP- and $Ca^{++}$—sensitive channels. Nearly identical results were obtained with 2-chlorophenyl-bis-phenyl methanol. clotrimazole and its metabolite 2-chlorophenyl-bis-phenyl methanol inhibit directly both cAMP- and $Ca^{++}$-sensitive intestinal K+ channels indicating that the ring structure in the absence of the imidazole ring sufficient (and perhaps necessary) for this bioactivity.

4. Clotrimazole Targets the Basolateral Rather than the Apical Surface of T84 Cells Methods Measurement of $Cl^-$ Conductance of the Apical Plasma Membrane: To examine apical Cl— conductances, $Cl^-$ was used as the sole permeant ion using identical apical and basolateral buffer solutions. Monolayers were pemeabilized basolaterally by the addition of 100 $\mu M$ Amphotericin B to the serosal reservoir. Generation of voltage-current curves of channel currents were elicited by 1 sec test potentials from −80 to +80 mV in 10 mV increments in symmetrical high Choline $Cl^-$ buffers.

Results

Studies were performed to determine whether the primary target of clotrimazole was located on the basoolateral or apical cell surfaces. Most rapid inhibition was achieved by incubation with clotrimazole on both sides of the monolayer. However, basolateral application alone was almost as effective as incubation on both sides. Additionally, the apparent potency of inhibition of clotrimazole at a fixed time point was found to be greater when applied basolaterally than apically. This preferential action of clotrimazole at the basolateral surface of the cell is consistent with the hypothesis that its principal targets are basolateral K+ channels.

To confirm these findings, we examined Cl— transport in T84 cell monolayers 30 permeabilized basolaterally with pores formed by amphotericin B. These studies were performed with Cl— as the only permeant anion, and with symmetrical apical and basolateral Cl— concentrations (142 mM). In monolayers not treated with clotrimazole, the addition of forskolin (10 $\mu M$) to basolateral reservoirs increased Cl— conductances significantly over baseline, presumably via activation of the cystic fibrosis transmembrane regulator (CFTR) Cl-channel. In contrast to the clear inhibitory effects of clotrimazole on basolateral $K^+$ conductances, however, clotrimazole had no detectable effect on either forskolin- or thapsigargin-stimulated Cl—conductances. I/V relations for Cl— transport were nearly identical in monolayers treated or not treated with clotrimazole. These data provide further evidence that clotrimazole inhibits Cl— secretion in intact T84 cell monolayers by affecting specifically basolateral K+ channels. Apical membrane Cl-channels are not inhibited.

Example 5

Clotrimazole Inhibits $Cl^-$ Secretion in vivo

1. Ussing Chamber Studies Using Rabbit Colonic Mucosa:

Methods 4 male, New Zealand rabbits (2.5 kg) were anesthetized by an intravenous injection of pentobarbital (0.5 ml/kg). A 15 cm length of distal colon was removed and opened longitudinally. External muscle layers were removed by blunt dissection and colonic mucosal preparations were mounted in an Ussing chamber (DCTSYS; Precision Instrument Design, CA; 10.3 $cm^2$ surface area) and incubated with buffer solution containing (in mM): NaCl 122.0, $CaCl_2$, 2.0; $MgSO_4$,1.3; KCl, 5.0, glucose, 20; $NaHCO_3$, 25.0 (pH when gassed with 95% O2/5 $CO_2$; temperature was maintained at 37° C.) with and without clotrimazole (30 $\mu M$). The volume of fluid on each side of the mucosa was 7 ml.

Potential difference and Isc were monitored continuously and registered every 10 minutes. Luminal and serosal buffer solutions were interfaced via Ag—AgCl electrodes (Voltage/Current Clamp, Model VCC600, Physiologic Instruments, Inc., San Diego, Calif., USA) and Ringer/agar bridge to voltage clamp device (model DVC-1000; Voltage/Current Clamp, World Precision Instruments, Inc.). Resistance (R) was calculated using Ohm's law and the Isc and is given in Ω×cm2. After stable baseline resistance and Isc values had been obtained, mucosal preparations were incubated in the presence or absence of serosal clotrimazole (30 $\mu M$) for 30 min, and then stimulated by the addition of forskolin (10 $\mu M$) or carbachol (10 $\mu M$) to the serosal reservoir.

Results

To test the ability of clotrimazole to block K+ channels and thus Cl— secretion in native intestinal tissue, we mounted isolated preparations of rabbit colonic mucosa in Ussing chambers containing modified Ringer's solution with or without clotrimazole (30 μM). After Isc had stabilized, successive additions of forskolin (10 μM) and then cubachol (100 μM) were applied to serosal reservoirs, and Isc and G were monitored continuously. clotrimazole inhibited strongly the time course of forskolin induced Isc. Carbachol had no further effect on Isc in this system.

2. Murine Model of Secretotory Diarrhea:

Methods

Treated and control, untreated, mice were gavage fed either clotrimazole (150 mg/kg/day divided in two equal doses, dissolved in peanut oil at a concentration of 20 mg/ml) or vehicle control over a 7 day loading period. Mice were then challenged by gavage with either 25 μg purified cholera toxin (Calbiochem, San Diego, Calif.) in PBS, vehicle control alone (PBS without cholera toxin), or cholera toxin in PBS containing 30 μM clotrimazole. Animals were sacrificed after 5 hours in an uncrowded $CO_2$ hood. The carcass was weighed, the abdomen was opened, and ligatures were tied at the proximal duodenum and distal rectum. The intestinal block was dissected free of supporting structures and removed as a single unit and weighed. Small and large intestinal segments were normalized to body weight (intestinal weight/carcass weight) for each animal.

Results

To examine whether clotrimazole may inhibit intestinal secretion in vivo, we utilized a murine model of secretary diarrhea. Balb/C mice were gavage fed 150 mg/kg/day clotrimazole, divided into two equal doses, or vehicle control every 12 h for 7 days and subsequently challenged orally with purified cholera toxin (25 μg). Five hours after treatment with cholera toxin, the mice were sacrificed and intestinal fluid secretion assessed gravimetrically. Pretreatment with clotrimazole reduced by 86% intestinal fluid secretion induced by cholera toxin. Clotrimazole had no effect on intestinal secretion in the absence of cholera toxin. Thus, clotrimazole effectively treated secretory diarrhea in vivo, presumably by inhibiting basolateral K+ channels of crypt epithelial cells.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

Each of the foregoing patents, patent applications and references is herein incorporated by reference in its entirety.

We claim:

1. A method for treating diarrhea, comprising, administering an effective amount for inhibiting Cl⁻ secretion of an aromatic compound to a subject, wherein the aromatic compound has the general formula:

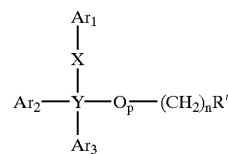

or a pharmaceutically acceptable salt or hydrate thereof, wherein:

n is 0, 1, 2, 3 or 4;

p is 0 or 1;

X is absent, ($C_1$–$C_3$)alkyl, ($C_1$–$C_3$)alkenyl, ($C_1$–$C_3$) alkynyl, $SCH_2$, $OCH_2$, or $NOCH_2$;

Y is C, N, P, Si or Ge;

R' is -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH aryl, or heteroaryl;

$Ar_1$ is aryl, substituted aryl, heteroaryl, ($C_5$–$C_8$)cycloalkyl or ($C_5$–$C_8$)heterocycloalkyl;

$Ar_2$ is aryl or substituted aryl;

$Ar_3$ is aryl, substituted aryl, biaryl, biphenyl, bibenzyl, or heteroaryl other than imidazole, nitroimidazole and triazole;

each R is independently selected from the group consisting of —H, ($C_1$–$C_6$)alkyl, substituted ($C_1$–$C_6$)alkyl, ($C_1$–$C_6$)alkenyl, substituted ($C_1$–$C_6$)alkenyl($C_1$–$C_6$) alkynyl, substituted ($C_1$–$C_6$)alkynyl, and ($C_1$–$C_6$) alkoxy; the aryl substituents are each independently selected from the group consisting of -halo, trihalomethyl, —R, —$R_1$, —$OR_1$, —$SR_1$, $NR_{12}$, —$NO_2$, —CN, —C(O)R, —C(S)$R_1$, —C(O)$R_1$, —C(S)$OR_1$, —C(O)SR, and —C(S)$SR_1$; the alkyl, alkenyl and alkynyl substituents are each independently selected from the group consisting of -halo, —$R_1$, —$OR_1$, —$SR_1$, N($R_1$)$_2$, —$NO_2$, —CN, —C(O) $R_{12}$, —C(S)$R_1$, —C(O)$OR_1$, —C(S)$OR_1$, —C(O)$SR_1$, —C(S)$SR_1$, aryl, γ-butyrolactonyl, pyrrolidinyl and succinic anhydridyl; and each $R_1$ is independently selected from the group consisting of —H, ($C_1$–$C_6$) alkyl, ($C_1$–$C_6$)alkenyl and ($C_1$–$C_6$)alkynyl, and provided that neither $Ar_1$ nor $Ar_3$ are oxadiazolyl when X is absent, Y is C, p=O, n=1–4, and R'=NR2.

2. The method of claim 1, wherein the aromatic compound is not any compound encompassed by formula (II):

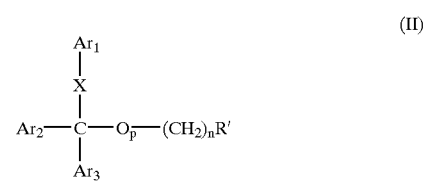

(II)

wherein n=0–3; wherein p=0 or 1; wherein X is selected from the group consisting of $(CH_2)_{m(m=0,1,2, or 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2$H, $CO_2$R", OR", SR", NR"R", CONR"R", heteroaryl, and CONR"($OCH_3$); wherein $Ar_1$ is selected from the group consisting of phenyl, substituted phenyl, and heteroaryl; wherein $Ar_2$ is selected from the group consisting of phenyl and substituted phenyl; wherein $Ar_3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=1-5)}$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, SH, $SCH_3$, $NH_2$, $NHCH_3$, and $N(CH_3)_2$; and wherein R" is selected from the group consisting of hydrogen and R.

3. The method of claim 1, wherein the aromatic compound is selected from the group consisting of aromatic compounds wherein p=0, X is absent, $(C_1-C_3)$alkyl, $(C_1-C_3)$alkenyl, $(C_1-C_3)$ or alkynyl; R' is absent, -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]—CH[C(S)R]$_2$, —CH[C(O)OR]$_2$, —CH[C(S)OR]$_2$, —CH[C(O)SR]$_2$, —CH[C(S)SR]$_2$, or aryl; $Ar_1$ is aryl, substituted aryl, heteroaryl other than imidazole, nitroimidazole and triazole, heteroarylium other than imidazolium, nitroimidazolium and triazolium, $(C_5-C_8)$cycloalkyl or $(C_5-C_8)$heterocycloalkyl; $Ar_2$ is aryl or substituted aryl; and $Ar_3$ is aryl, substituted aryl, biaryl, or heteroaryl other than imidazole, nitroimidazole and triazole.

4. The method of claim 2, wherein the aromatic compound is administered orally.

5. The method of claim 2, wherein the subject is a human.

6. The method of claim 5, further comprising administering an anti-diarrheal agent to the subject.

7. The method of claim 6, wherein the anti-diarrheal agent is an oral rehydration fluid.

8. The method of claim 1, wherein the aromatic compound is selected from the group consisting of:

(7)

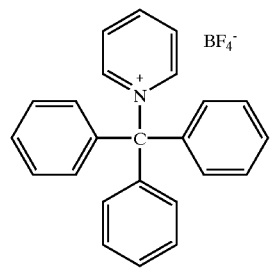

(10)

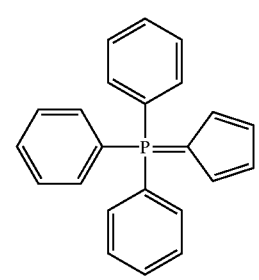

(12)

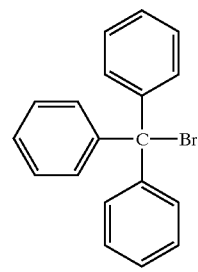

(13)

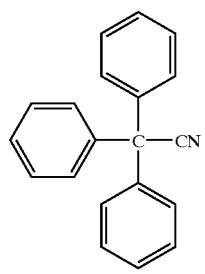

(14)

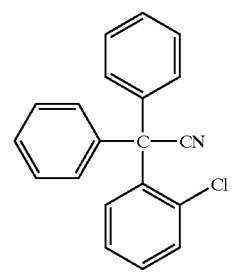

(15)

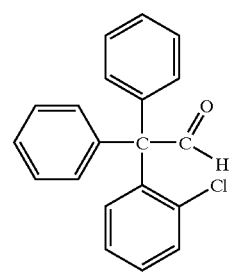

(16)

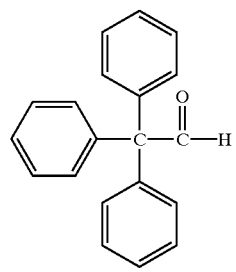

(18)

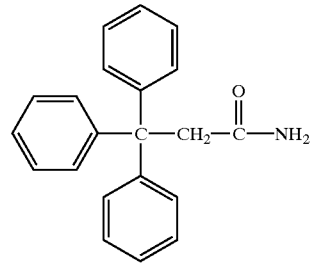

(20) triphenyl(2-fluorophenyl)methanol

(21) [1,1'-biphenyl]-4-yl-diphenylmethanol

(22) 3,3,3-triphenylpropan-1-ol

(23) (5S)-5-[(trityloxy)methyl]pyrrolidin-2-one

(24) (5S)-5-[(trityloxy)methyl]dihydrofuran-2(3H)-one

(27) (2-fluorophenyl)diphenylmethane

(29) 2,2,2-triphenylethylamine

(30) 3,3,3-tris(4-chlorophenyl)propanamide

(31) diethyl 2-(triphenylmethyl)malonate [CPh₃-CH(CO₂CH₂CH₃)₂]

(32) (2-fluorophenyl)diphenylacetonitrile

(33) diethyl 2-[(2-chlorophenyl)(diphenyl)methyl]malonate

-continued
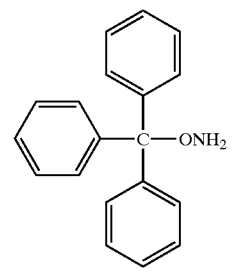
(34)
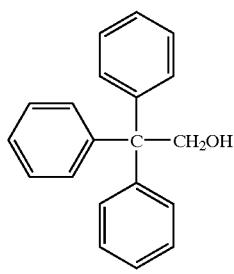
(35)
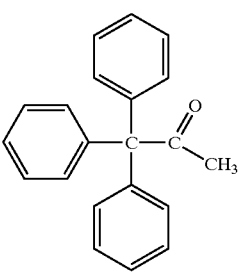
(37)
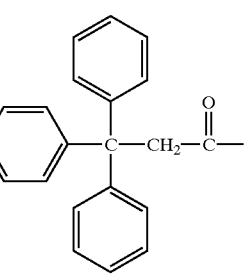
(38)
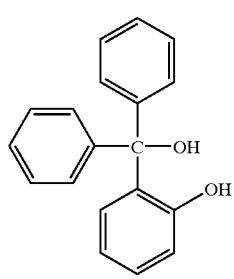
(42)
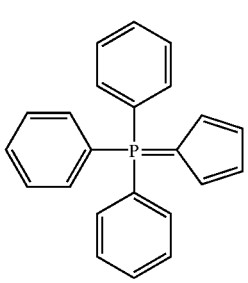
(43)
-continued
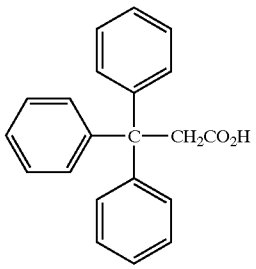
(44)
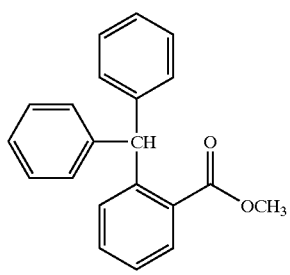
(45)
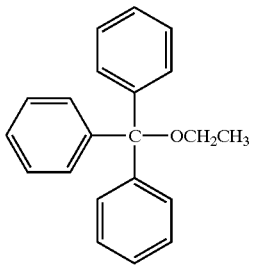
(46)
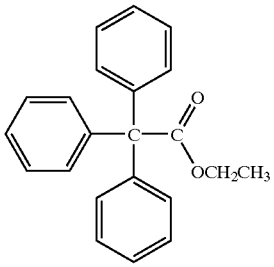
(47)
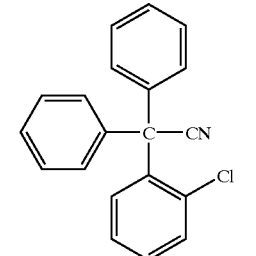
(49)

-continued
(50)
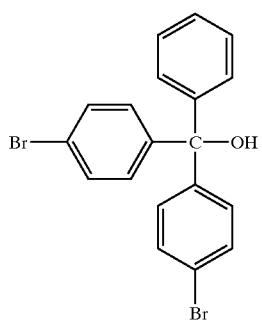
(51)
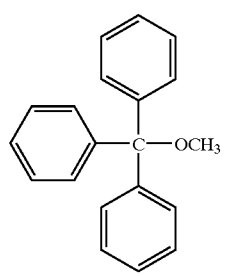
(52)
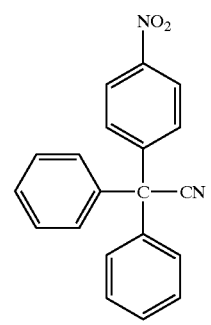
(53)
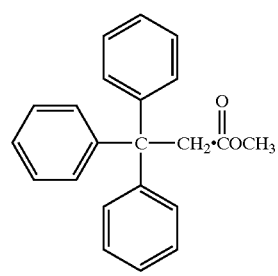
(55)
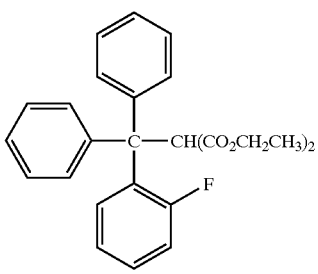
-continued
(56)
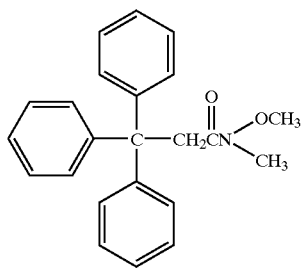
(58)
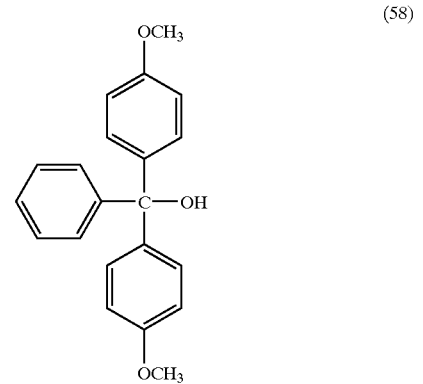
(59)
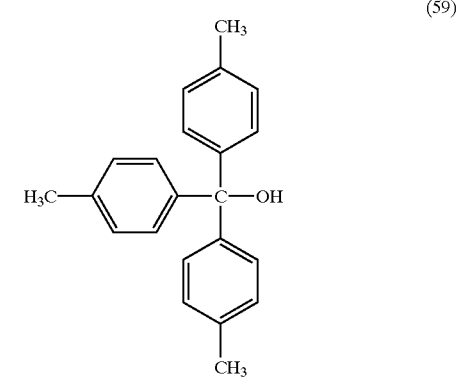
(60)
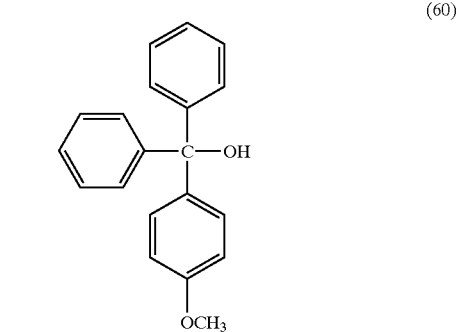

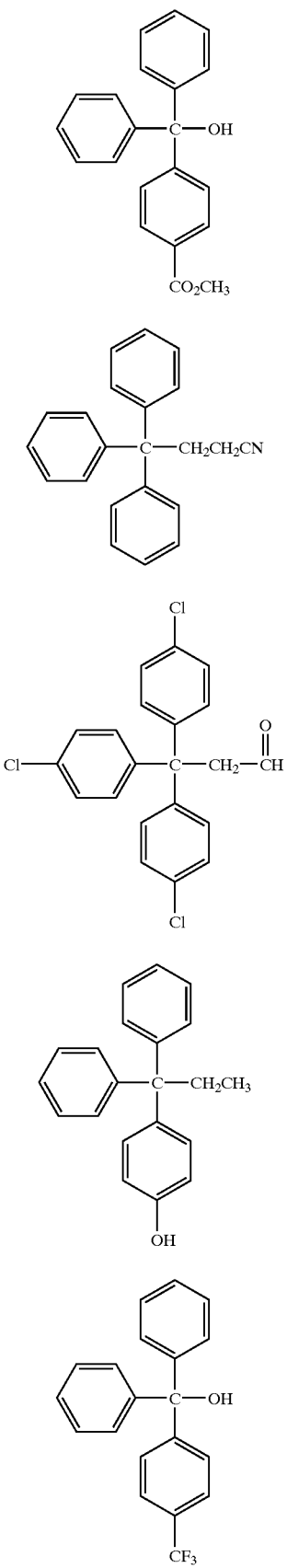
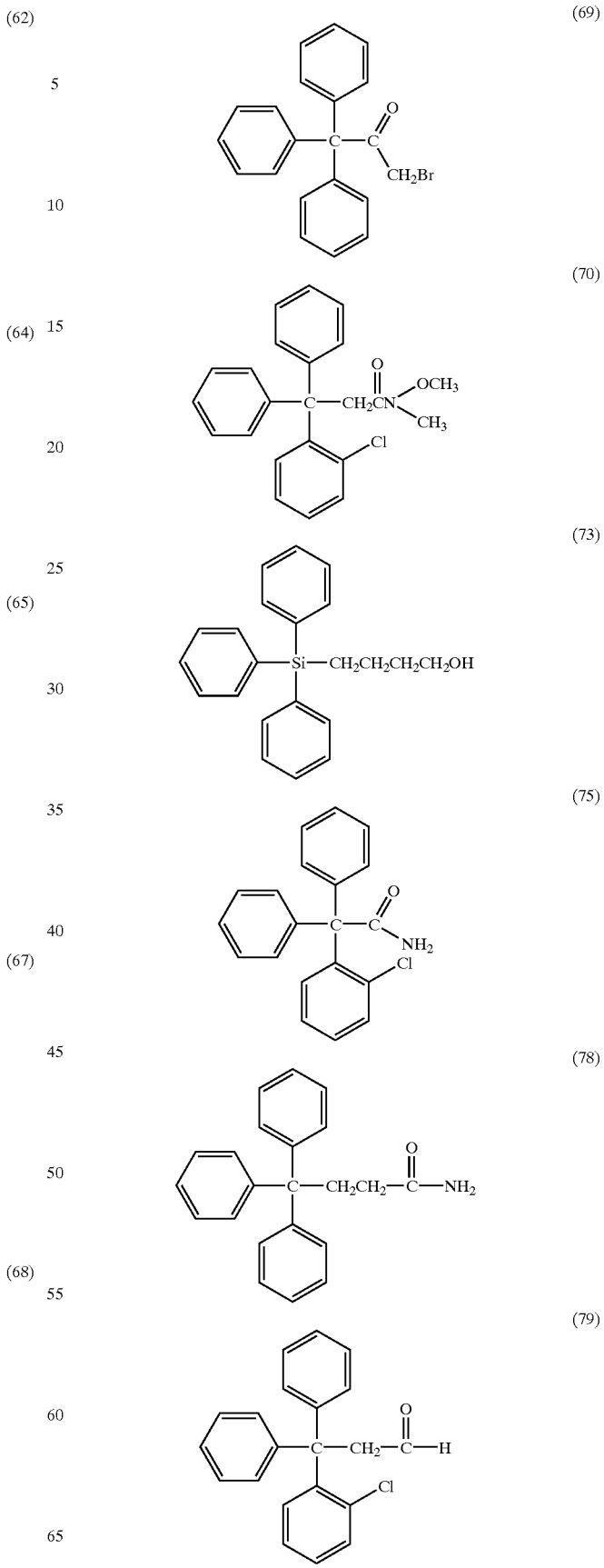

-continued

(80) 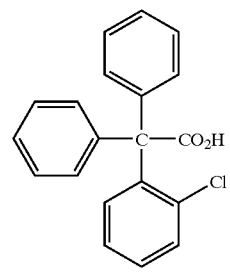

(81) 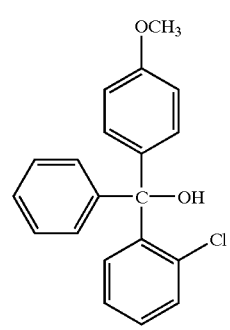

(82) 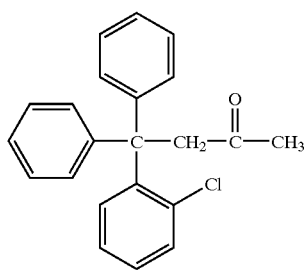

(83) 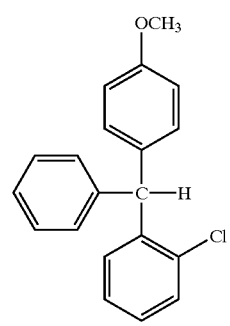

(86) 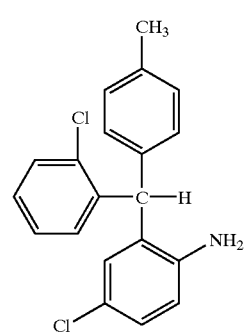

-continued

(87) 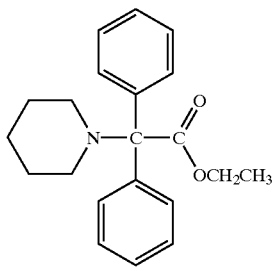

(88) 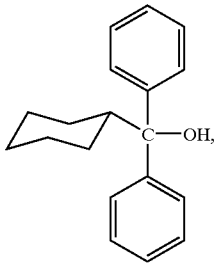

and

(90) 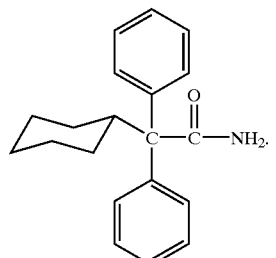

9. A method for treating scours, the method comprising the step of: administering to a subject in need of such treatment, an aromatic compound in an amount effective to inhibit scours, wherein the aromatic compound has the general formula:

(I) 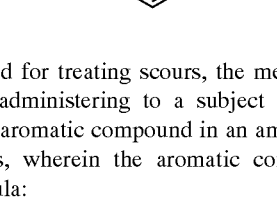

or a pharmaceutically acceptable salt or hydrate thereof, wherein:

n is 0, 1, 2, 3 or 4;

p is 0 or 1;

X is absent, $(C_1-C_3)$alkyl, $(C_1-C_3)$alkenyl, $(C_1-C_3)$alkynyl, $SCH_2$, $OCH_2$, or $NOCH_2$;

Y is C, N, P, Si or Ge;

R' is -halo, —R, —OR, —SR, —$NR_2$, —$ONR_2$, —$NO_2$, —CN, —C(O)R, —C(S)R, —C(O)OR, —C(S)OR, —C(O)SR, —C(S)SR, —C(O)$NR_2$, —C(S)$NR_2$, —C(O)NR(OR), —C(S)NR(OR), —C(O)NR(SR), C(S)NR(SR), —CH(CN)$_2$, —CH[C(O)R]$_2$, —CH[C(S)R]$_2$, —CH[C(O)OR]$_2$, —CH[C(S)OR]$_2$, —CH[C(O)SR]$_2$, —CH[C(S)SR]$_2$, aryl, or heteroaryl;

$Ar_1$ is aryl, substituted aryl, heteroaryl, $(C_5-C_8)$cycloalkyl or $(C_5-C_8)$heterocycloalkyl;

$Ar_2$ is aryl or substituted aryl;

$Ar_3$ is aryl, substituted aryl, biaryl, biphenyl, bibenzyl, or heteroaryl other than imidazole, nitroimidazole and triazole;

each R is independently selected from the group consisting of —H, $(C_1-C_6)$alkyl, substituted $(C_1-C_6)$alkyl, $(C_1-C_6)$alkenyl, substituted $(C_1-C_6)$alkenyl$(C_1-C_6)$ alkynyl, substituted $(C_1-C_6)$alkynyl, and $(C_1-C_6)$ alkoxy; the aryl substituents are each independently selected from the group consisting of -halo, trihalomethyl, —R, —$R_1$, —$OR_1$, —$SR_1$, $NR_{12}$, —$NO_2$, —CN, —C(O)$R_1$, —C(S)$R_1$, —C(O)$OR_1$, —C(S)$OR_1$, —C(O)$SR_1$ and —C(S)$SR_1$; the alkyl, alkenyl and alkynyl substituents are each independently selected from the group consisting of -halo, —$R_1$, —$OR_1$, —$SR_1$, $N(R_1)_2$, —$NO_2$, —CN, —C(O) $R_1$, —C(S)$R_1$, —C(O)$OR_1$, —C(S)$OR_1$, —C(O)$SR_1$, —C(S)$SR_1$, aryl, γ-butyrolactonyl, pyrrolidinyl and succinic anhydridyl; and each $R_1$ is independently selected from the group consisting of —H, $(C_1-C_6)$ alkyl, $(C_1-C_6)$alkenyl and $(C_1-C_6)$alkynyl, and provided that neither $Ar_1$ nor $Ar_3$ are oxadiazolyl when X is absent, Y is C, p=0, n=1–4, and R'=NR2.

10. The method for treating scours as in claim 1, wherein the aromatic compound is not any compound encompassed by formula (II):

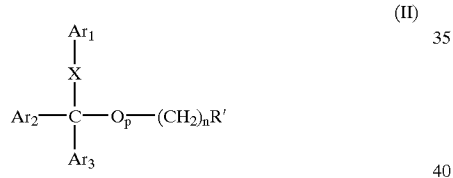
(II)

wherein n=0–3; wherein p=0 or 1; wherein X is selected from the group consisting of $(CH_2)_{m(m=0,1,2, or 3)}$, CH=CH, C≡C, $SCH_2$, $OCH_2$, and $NOCH_2$; wherein R' is selected from the group consisting of H, OH, SH, $NO_2$, CN, CHO, $ONH_2$, CCH, COR", $CO_2H$, $CO_2R$", OR", SR", NR"R", CONR"R", heteroaryl, and CONR"($OCH_3$); wherein $Ar_1$ is selected from the group consisting of phenyl, substituted phenyl, and heteroaryl; wherein $Ar_2$ is selected from the group consisting of phenyl and substituted phenyl; wherein $Ar_3$ is selected from the group consisting of phenyl, substituted phenyl, biphenyl, bibenzyl, and naphthyl; wherein the phenyl substituent is selected from the group consisting of Cl, F, Br, I, R, OR", SR", $NO_2$, CN, $CF_3$, NR"R", and $CO_2R$; wherein R is selected from the group consisting of straight chain alkyl of $C_{z(z=1-5)}$, substituted straight chain alkyl of $C_{z(z=1-5)}$, branched alkyl of $C_{z(z=1-5)}$, and substituted branched alkyl of $C_{z(z=1-5)}$; wherein the alkyl substituent is selected from the group consisting of Cl, Br, F, I, OH, $OCH_3$, SH, $SCH_3$, $NH_2$, $NHCH_3$, and $N(CH_3)_2$; and wherein R" is selected from the group consisting of hydrogen and R.

11. The method for treating scours as in claim 9, wherein the aromatic compound is selected from the group consisting of

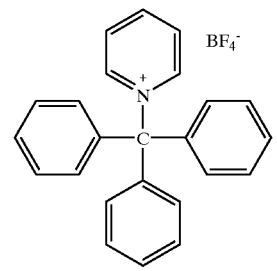
(7)

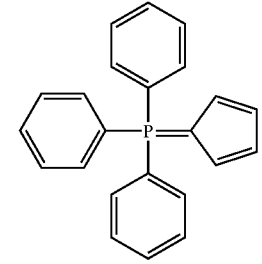
(10)

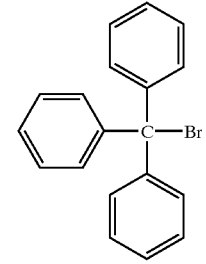
(12)

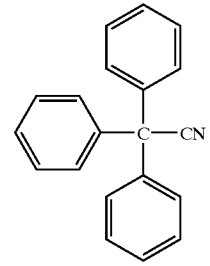
(13)

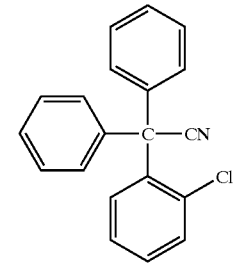
(14)

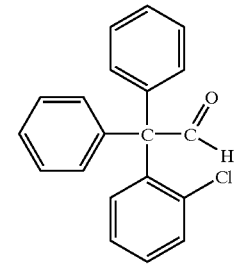
(15)

(16)
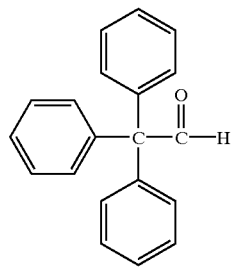
(18)
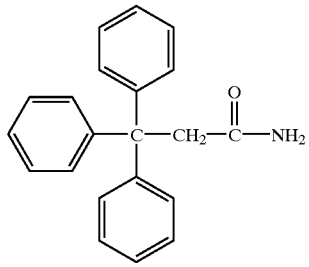
(20)
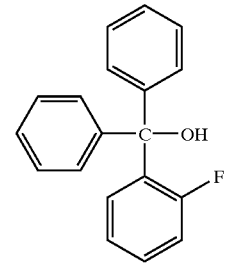
(21)
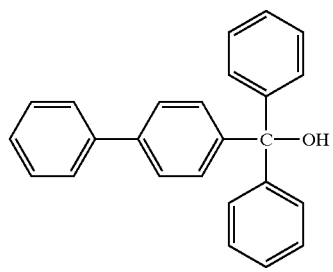
(22)
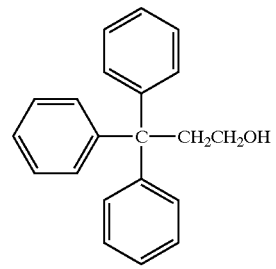
(23)
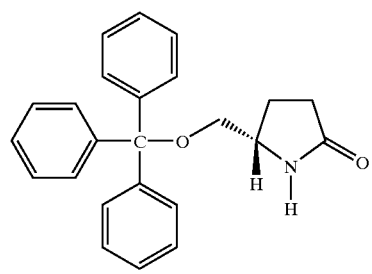
(24)
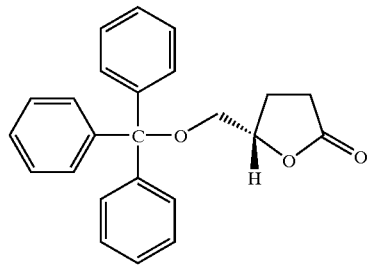
(27)
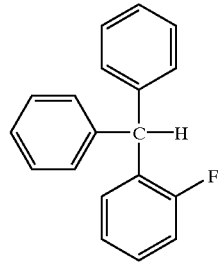
(29)
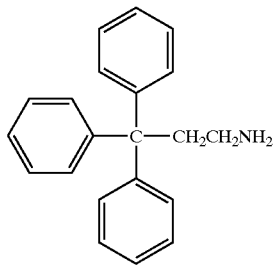
(30)
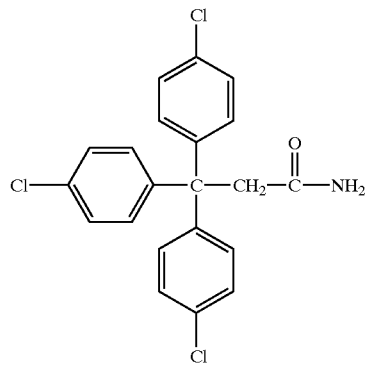
(31)
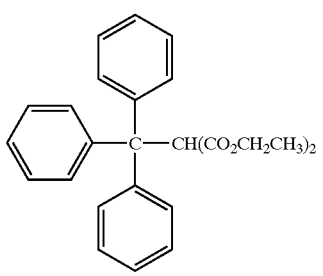

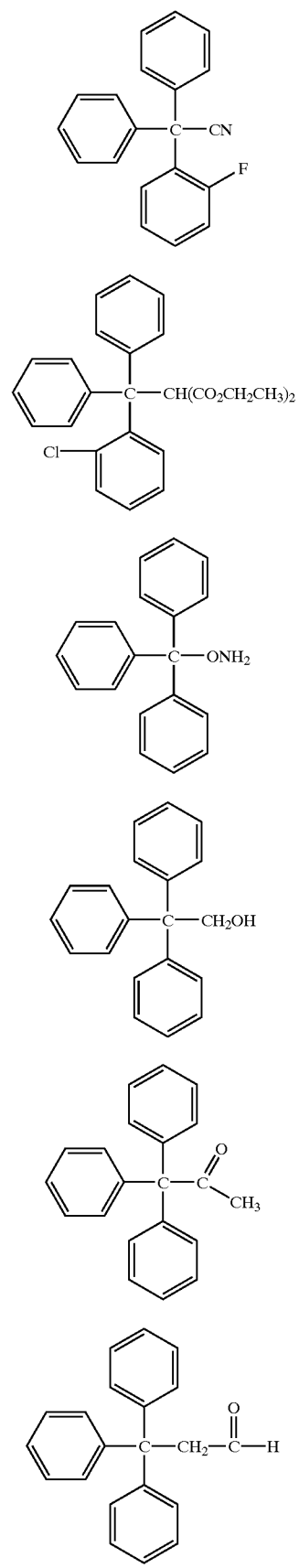
(32)
(33)
(34)
(35)
(37)
(38)
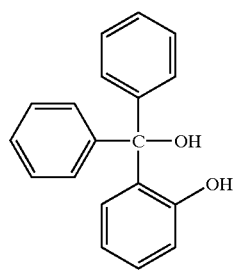
(42)
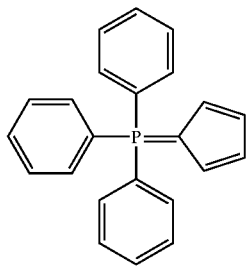
(43)
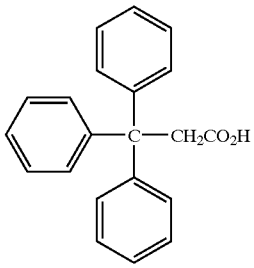
(44)
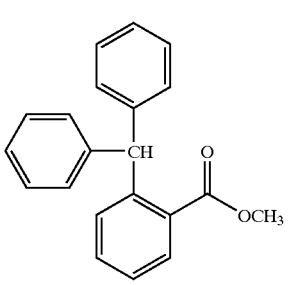
(45)
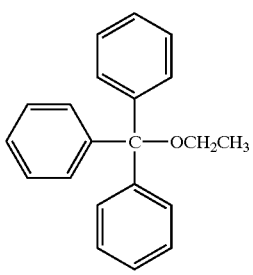
(46)
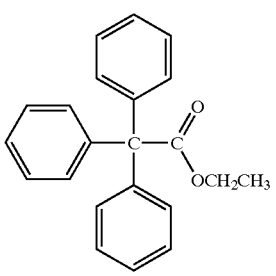
(47)

(49) 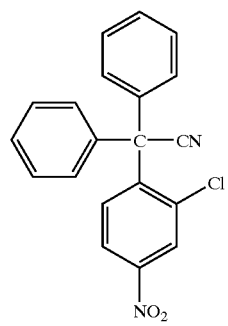
(50) 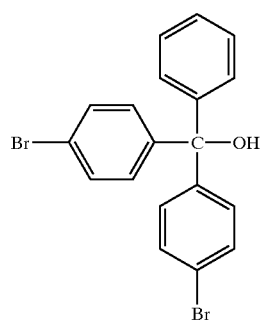
(51) 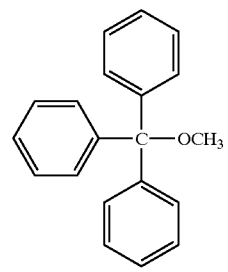
(52) 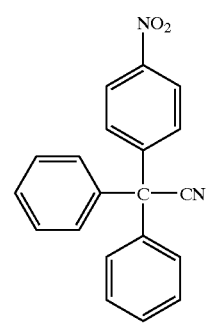
(53) 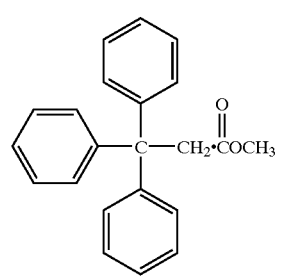
(55) 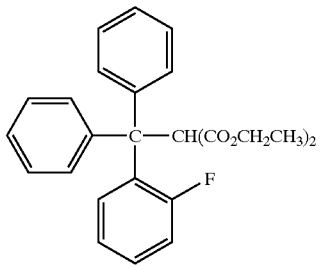
(56) 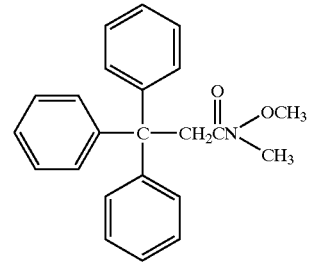
(58) 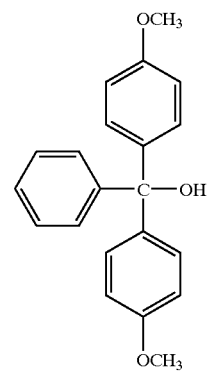
(59) 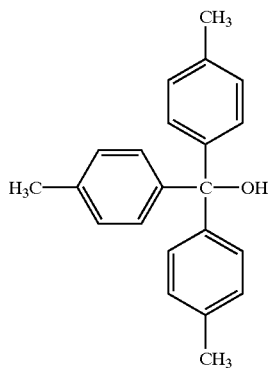
(60) 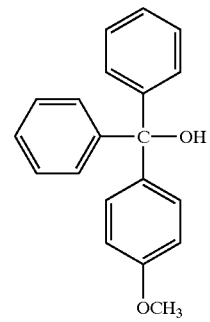

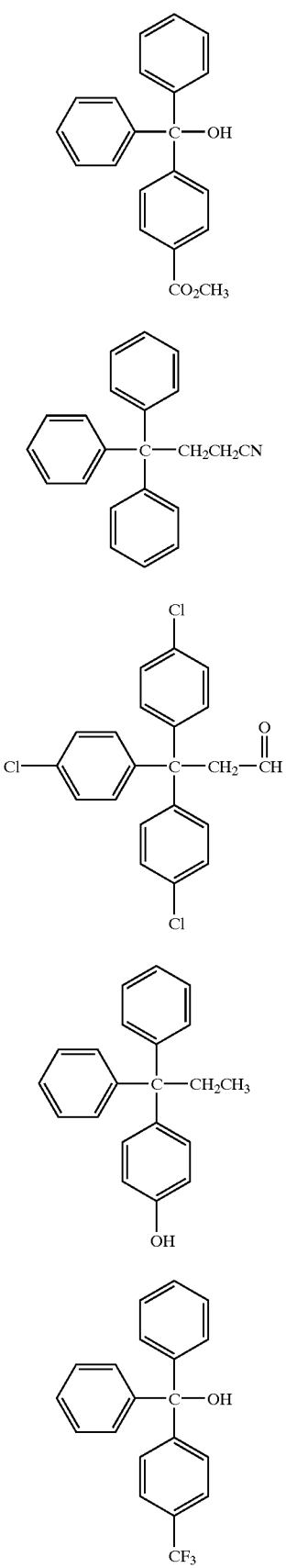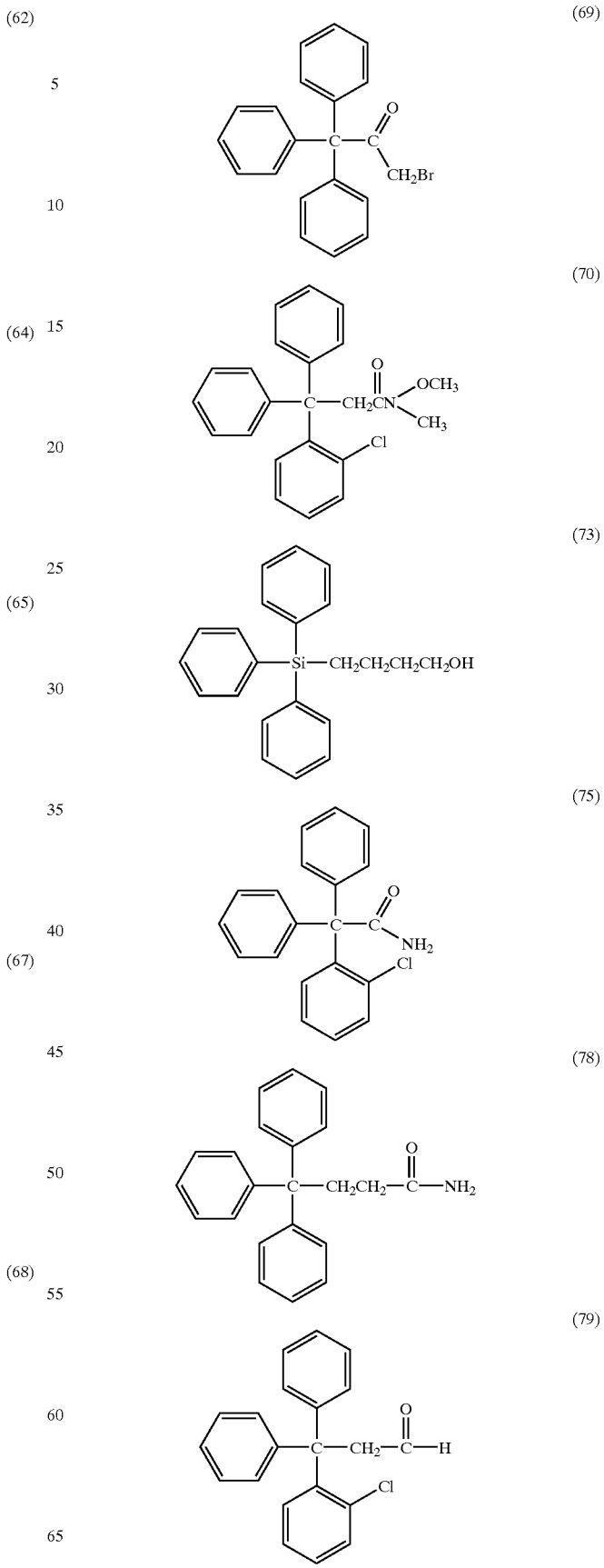

(80)
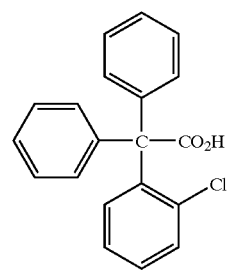
(81)
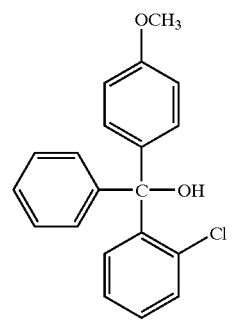
(82)
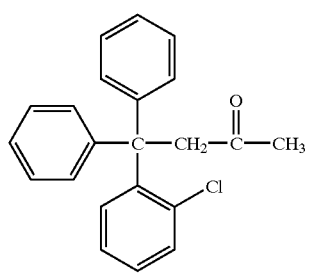
(83)
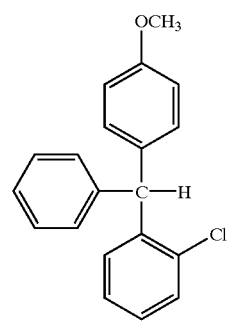
(86)
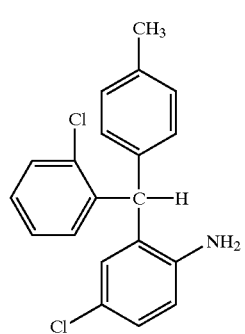
(87)
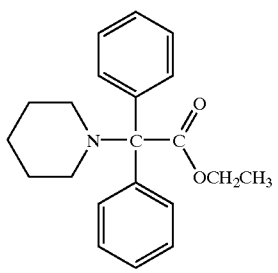
(88)
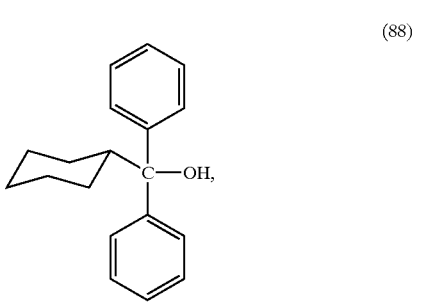
and
(90)
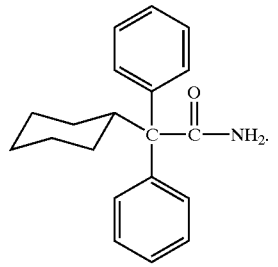
12. The method for treating scours as in claim 9, wherein the aromatic compound is administered orally.
13. The method for treating scours as in claim 9, wherein the subject is selected from the group consisting of a horse, a cow, a pig, and a goat.
14. The method for treating scours as in claim 9, further comprising administering an anti-scours agent to the subject.
* * * * *

UNITED STATES PATENT AND TRADEMARK OFFICE
CERTIFICATE OF CORRECTION

PATENT NO.   : 6,495,567 B1
DATED        : December 17, 2002
INVENTOR(S)  : Lencer et al.

It is certified that error appears in the above-identified patent and that said Letters Patent is hereby corrected as shown below:

Column 35,
Line 59, delete the word "glucase" and replace with the word -- glucose --.

Column 37,
Line 33, delete the word "secretory" and replace with the word -- Secretory --.

Column 40,
Line 61, delete the word "Nemst-potential" and replace with the word -- Nernst-potential --.

Column 41,
Line 7, delete the word "(Nea)" and replace with the word -- $Na^+$ --.

Column 57,
Line 30, delete "1" and replace with -- 9 --.

Signed and Sealed this

Twenty-ninth Day of April, 2003

JAMES E. ROGAN
*Director of the United States Patent and Trademark Office*